US011510911B2

United States Patent
Woo et al.

(10) Patent No.: US 11,510,911 B2
(45) Date of Patent: Nov. 29, 2022

(54) METHOD FOR PREDICTION OF SUSCEPTIBILITY TO SORAFENIB TREATMENT BY USING SULF2 GENE, AND COMPOSITION FOR TREATMENT OF CANCER COMPRISING SULF2 INHIBITOR

(71) Applicant: AJOU UNIVERSITY INDUSTRY—ACADEMIC COOPERATION FOUNDATION, Suwon-si (KR)

(72) Inventors: Hyun Goo Woo, Suwon-si (KR); Sarah Yoon, Yongin-si (KR); Eun-Ju Lee, Hwaseong-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 50 days.

(21) Appl. No.: 16/495,555

(22) PCT Filed: Mar. 20, 2018

(86) PCT No.: PCT/KR2018/003201
§ 371 (c)(1),
(2) Date: Sep. 19, 2019

(87) PCT Pub. No.: WO2018/174506
PCT Pub. Date: Sep. 27, 2018

(65) Prior Publication Data
US 2020/0085802 A1 Mar. 19, 2020

(30) Foreign Application Priority Data
Mar. 20, 2017 (KR) .................. 10-2017-0034642

(51) Int. Cl.
| | |
|---|---|
| *A61K 31/44* | (2006.01) |
| *A61K 39/395* | (2006.01) |
| *C12N 15/113* | (2010.01) |
| *A61K 45/06* | (2006.01) |
| *C12Q 1/6886* | (2018.01) |
| *G01N 33/574* | (2006.01) |

(52) U.S. Cl.
CPC .......... *A61K 31/44* (2013.01); *A61K 39/3955* (2013.01); *A61K 45/06* (2013.01); *C12N 15/113* (2013.01); *C12Q 1/6886* (2013.01); *G01N 33/574* (2013.01); *C12Q 2525/207* (2013.01); *C12Q 2600/106* (2013.01); *C12Q 2600/156* (2013.01); *C12Q 2600/158* (2013.01)

(58) Field of Classification Search
CPC .............. C12N 15/113; A61K 39/3955; C12Q 2525/207; C12Q 2600/106
See application file for complete search history.

(56) References Cited

U.S. PATENT DOCUMENTS

2006/0063230 A1* 3/2006 Naworth ............ A61K 38/1816
435/69.1

FOREIGN PATENT DOCUMENTS

| KR | 10-2017-0095107 A | 8/2017 |
| KR | 10-1793175 B1 | 11/2017 |
| WO | 2012/106192 A1 | 8/2012 |

OTHER PUBLICATIONS

Llovet et al (J Clin Oncol 31:3509-3516) (Year: 2013).*
Allen et al (Clin Cancer Res; 17(16): 5299-5310, 2011) (Year: 2011).*
Takashima et al (Am J Physiol Renal Physiol 310: F395-F408, 2016) (Year: 2016).*
Rosen et al (Expert Opin. Ther. Targets (2010) 14(9): 935-949) (Year: 2010).*
Machine translation of KR20170095107A, downloaded from https://patents.google.com/patent/KR20170095107A/en on Jul. 12, 2021 (Year: 2017).*
De Souza et al (PLoS ONE 10(8): e0134276, 2015) (Year: 2015).*
Yoon et al (Oncogene (2018) 37:4443-4454) (Year: 2018).*
Kim, Tae Hyung, "Double-Diagnostic Diagnosis, Liquid Biopsy . . . " Domestic Cancer Genome, Biospectator, Feb. 22, 2017, Internet <http://www.biospectator.com/view/news_view.php?varAtcld=2786>, total 4 pages.
Alhasan, S. F. et al., "PMO-094 Suppression of SULF2, An Extracellular Endosulfatase up-Regulated in Hepatocellular Cancers, Modulates WNT Signalling And Inhibits Cell Growth", Gut, Jul. 2012, vol. 61, Suppl. 2, pp. A111-A1112 (total 3 pages).
Zheng Xin et al., "The Human Sulfatase 2 Inhibitor 2,4-Disulfonylphenyl-tert-Butylnitrone (OKN-007) has an Antitumor Effect in Hepatocellular Carcinoma Medicated via Suppression of TGFB1/SMAD2 and Hedgehog/GLI1 Signaling", Genes Chromosomes Cancer, Mar. 2013, vol. 52, No. 3, pp. 225-236 (total 19 pages).

(Continued)

*Primary Examiner* — Richard A Schnizer
(74) *Attorney, Agent, or Firm* — Sughrue Mion, PLLC

(57) ABSTRACT

The present invention relates to a method for predicting susceptibility to sorafenib treatment by using an SULF2 gene, and a composition for treatment of sorafenib-resistant cancer using the SULF2 expression inhibition. The method for predicting susceptibility to sorafenib treatment by using the SULF2 gene according to the present invention can enable achievement of an optimal therapeutic effect by administering a drug suitable for cancer patients, and the composition for treatment of sorafenib-resistant cancer using the SULF2 inhibition has a very excellent anticancer treatment effect.

4 Claims, 19 Drawing Sheets
Specification includes a Sequence Listing.

(56) References Cited

OTHER PUBLICATIONS

Vicente Carolina M. et al., "SULF2 overexpression positively regulates tumorigenicity of human prostate cancer cells", Journal of Experimental & Clinical Cancer Research, 2015, vol. 34, No. 25, pp. 1-16 (total 16 pages).
Basu Amrita et al., "An interactive resource to identify cancer generic and lineage dependencies targeted by small molecules", Cell, Aug. 29, 2013, vol. 154, No. 5, pp. 1151-1161 (total 20 pages).
Iorio Francesco et al., "A Landscape of Pharmacogenomic Interactions in Cancer", Cell, 2016, vol. 166, pp. 740-754 (total 16 pages).
Stratton, Michael R. et al., "The Cancer Genome", Nature, Apr. 9, 2009, vol. 458, No. 7239, pp. 719-724 (total 16 pages).
Vivès, Romain R. et al., "Post-synthetic regulation of HS structure: the yin and yang of the Sulfs in cancer", Frontiers in Oncology, Jan. 2014, vol. 3, Article 331, pp. 1-11 (total 11 pages).
Lai, Jun-Ping, et al., "Sulfatase 2 Up-Regulates Glypican 3, Promotes Fibroblast Growth Factor Signaling, and Decreases Survival in Hepatocellular Carcinoma", Hepatology, Apr. 2008, vol. 47, No. 4, pp. 1211-1222 (total 21 pages).
Flower, D.R. et al., "Mouse oncogene protein 24p3 is a member of the Lipocalin protein family", Biochemical and Biophysical Research Communications, Oct. 15, 1991, vol. 180, No. 1, pp. 69-74, (total 6 pages).
Schlehuber, Steffen et al., "Keynote review: Lipocalins in drug discovery: from natural ligand-binding proteins to 'anticalins'," DDT, Jan. 2005, vol. 10, No. 1, pp. 23-33 (total 11 pages).
Leung, Lisa et al., "Lipocalin2 Promotes Invasion, Tumorigenicity and Gemcitabine resistance in Pancreatic Ductal Adenocarcinoma", Plos One, Oct. 2012, vol. 7, Issue 10, e46677, pp. 1-10 (total 10 pages).
Shiiba, Masashi et al., "Lipocalin-2 is associated with radioresistance in oral cancer and lung cancer cells", International Journal of Oncology, 2013, vol. 42, pp. 1197-1204 (total 8 pages).
Tovar, Victoria et al., Tumour initiating cells and IGF/FGF signalling contribute to sorafenib resistance in hepatocellular carcinoma, Gut, Mar. 2017, vol. 66, No. 3, pp. 530-540 (total 21 pages).
Rudalska, Ramona et al., "In vivo RNAi screening identifies a mechanism of sorafenib resistance in liver cancer", Nat Med, Oct. 2014, vol. 20, No. 10, pp. 1138-1146 (total 22 pages).
Kuczynski, Elizabeth A. et al., "Effects of sorafenib dose on acquired reversible resistance and toxicity in hepatocellular carcinoma", Cancer Research, Apr. 23, 2015, total 30 pages.

Barretina, Jordi et al., The Cancer Cell Line Encyclopedia enables predictive modeling of anticancer drug sensitivity, Nature, Sep. 29, 2012, vol. 483, No. 7391, pp. 603-607 (total 13 pages).
Viau, Amandine et al., "Lipocalin 2 is essential for chronic kidney disease progression in mice and humans", The Journal of Clinical Investigation, Nov. 2010, vol. 120, No. 11, pp. 4065-4076 (total 12 pages).
Zhao, Peng et al., "STAT1, NF-κB and ERKs play a role in the induction of lipocalin-2 expression in adipocytes", Molecular Metabolism, 2013, vol. 2, pp. 161-170 (total 10 pages).
Xu, Ming-Jiang et al., "The liver is the major source of elevated serum lipocalin-2 levels after bacterial infection or partial hepatectomy: a critical role for IL-6/STAT3", Hepatology, Feb. 2015, vol. 61, No. 2, pp. 692-702 (total 20 pages).
Ding, Guanxiong et al., "Over-Expression of Lipocalin 2 Promotes Cell Migration and Invasion Through Activating ERK Signaling to Increase SLUG Expression in Prostate Cancer", The Prostate, 2015, pp. 1-12 (total 12 pages).
Marie-José Blivet-Van Eggelpoël et al., "Epidermal growth factor receptor and HER-3 restrict cell response to sorafenib in hepatocellular carcinoma cells", Journal of Hepatology, 2012, vol. 57, pp. 108-115 (total 8 pages).
Frese, Marc-André et al., "Characterization of the Human Sulfatase Sulf1 and Its High Affinity Heparin/Heparan Sulfate Interaction Domain", The Journal of Biological Chemistry, Oct. 9, 2009, vol. 284, No. 41, pp. 28033-28044 (total 12 pages).
Tang, Renhong et al., "Functional Consequences of the Subdomain Organization of the Sulfs", The Journal of Biological Chemistry, Aug. 7, 2009, vol. 284, No. 32, pp. 21505-21514 (total 11 pages).
Wang, Lihong et al., "A Novel Monoclonal Antibody to Fibroblast Growth Factor 2 Effectively Inhibits Growth of Hepatocellular Carcinoma Xenografts", Molecular Cancer Therapeutics, Apr. 2012, vol. 11, No. 4, pp. 864-872 (total 10 pages).
Sandhu, Dalbir S. et al., "Fibroblast Growth Factor Signaling in Liver Carcinogenesis", Hepatology, 2014, vol. 59, No. 3, pp. 1166-1173 (total 8 pages).
Berasain, Carmen, "Hepatocellular carcinoma and sorafenib: too many resistance mechanisms?", Gut, Dec. 2013, vol. 62, No. 12, pp. 1674-1675 (total 3 pages).
Chow, Ariel Ka-Man et al., "The Enhanced Metastatic Potential of Hepatocellular Carcinoma (HCC) Cells with Sorafenib Resistance", Plos One, Nov. 2013, vol. 8, Issue 11, e78675, pp. 1-10 (total 10 pages).
English Translation of International Search Report for PCT/KR2018/003201 dated Jun. 12, 2018.
English Translation of Written Opinion of the International Searching Authority for PCT/KR2018/003201 dated Jun. 12, 2018.

\* cited by examiner

METHOD FOR PREDICTION OF SUSCEPTIBILITY TO SORAFENIB TREATMENT BY USING SULF2 GENE, AND COMPOSITION FOR TREATMENT OF CANCER COMPRISING SULF2 INHIBITOR

CROSS REFERENCE TO RELATED APPLICATIONS

This application is a National Stage of International Application No. PCT/KR2018/003201 filed Mar. 20, 2018, claiming priority based on Korean Patent Application No. 10-2017-0034642 filed Mar. 20, 2017.

TECHNICAL FIELD

The present invention relates to a method of predicting susceptibility (sensitivity) to sorafenib treatment using SULF2 genes and a composition for treating sorafenib-resistant cancer using inhibition of SULF2 expression.

BACKGROUND ART

Currently, surgery, radiation therapy, chemotherapy and the like are used to treat cancer. In recent days, about 60 different types of anticancer drugs have come to be used, and research on the development of new anticancer drugs is actively underway. However, when anticancer drugs are administered repeatedly over a long period of time or cancer recurs, the anticancer drugs disadvantageously lose their therapeutic effects because cancer cells tend to acquire resistance to the anticancer drugs.

Therefore, the development of various types of anticancer drugs is continuously required due to the development of resistance thereto, and in particular, selective treatment with anticancer drugs that are capable of minimizing side effects of patients is required.

In conventional cancer chemotherapy, appropriate anticancer drugs are selected and administered depending on the type and severity of cancer, without consideration to individual cancer patients. However, general clinical results show that therapeutic effects of cancer chemotherapy differ greatly depending on the patient.

In order to overcome the drawbacks of the chemotherapy described above, it is required to identify drug-gene interactions using drug genomic data such as cancer cell line encyclopedia (CCLE), cancer genome project (CGP), connectivity map (CMAP) and NC170 panels, that is, to diagnose drug susceptibility in cancer cells and to identify a variety of drug candidates corresponding to specific genomic changes in respective tumors, including not only genetic mutations but also variations in transcription, methylation and number of DNA copies (Basu A et al., Cell 154:1151-61, 2013; Iorio F et al., Cell 166: 740-54, 2016). However, it is difficult to find a potential (possible) subject from hundreds of mutations, and it is thus difficult to develop a clinical therapy method from genome data, and careful and rigorous analysis to reduce errors entails the disadvantageous risk of discarding meaningful information.

Meanwhile, sorafenib is known as an oral multikinase inhibitor that treats cancers by attacking only cancer cells and vascular endothelial cells that supply nutrients to the cancer cells, while leaving normal cells intact. In recent years, sorafenib has been clinically researched for efficacy against various solid tumors and has been already used as a target anticancer drug for the treatment of renal cell carcinoma. Also, clinical research on the use of sorafenib to treat progressive hepatocellular carcinoma has been made, and sorafenib has been approved by the US Food and Drug Administration as a therapeutic agent for hepatocellular carcinoma to which resection is inapplicable.

However, there is a need for a method of predicting a therapeutic response prior to beginning of treatment and a method of identifying the same, since a plurality of patients are identified as being subjects who do not respond to the administration and treatment of sorafenib. In addition, the administration of appropriate drugs is possible through prediction of the susceptibility of subjects treated with sorafenib based on the study of reliable genomic biomarkers.

Therefore, as a result of extensive efforts to predict and improve susceptibility to sorafenib treatment in cancer patients through the systemic analysis of pharmacogenomic data, the present inventors have found that the SULF2-EGFR-LCN2 pathway plays an important role in determining susceptibility to sorafenib and resistance to liver cancer cells. Based on this finding, the present invention has been completed.

DISCLOSURE

Technical Problem

Therefore, the present invention has been made in view of the above problems, and it is an object of the present invention to provide a method of predicting susceptibility to sorafenib treatment by measuring the expression level of a SULF2 (sulfatase 2) gene or protein.

It is another object of the present invention to provide a composition for predicting susceptibility to sorafenib treatment containing an agent capable of measuring the expression level of a SULF2 (sulfatase 2) gene or protein, or an agent capable of detecting a SULF2 (sulfatase 2) mutant.

It is another object of the present invention to provide a pharmaceutical composition for treating cancer containing an agent capable of inhibiting expression of SULF2 (sulfatase 2).

It is another object of the present invention to provide a method of treating cancer including administering a composition containing an agent capable of inhibiting expression of SULF2 (sulfatase 2).

It is another object of the present invention to provide the use of a composition containing an agent capable of inhibiting expression of SULF2 (sulfatase 2) for the treatment of cancer.

Technical Solution

In accordance with one aspect of the present invention, the above and other objects can be accomplished by the provision of a method of predicting susceptibility to sorafenib treatment including (a) extracting DNA or protein from a sample isolated from a subject, (b) measuring an expression level of mRNA of a SULF2 (sulfatase 2) gene or a protein encoded by the gene, and (c) predicting that susceptibility to sorafenib treatment will be high when the expression level is reduced compared to a control group.

In accordance with another aspect of the present invention, there is provided a composition for predicting susceptibility to sorafenib treatment of a cancer patient containing an agent capable of measuring an expression level of mRNA of a SULF2 (sulfatase 2) gene or a protein encoded by the gene.

In accordance with another aspect of the present invention, there is provided a composition for predicting susceptibility to sorafenib treatment of a cancer patient containing an agent capable of detecting a SULF2 (sulfatase 2) mutant.

In accordance with another aspect of the present invention, there is provided a pharmaceutical composition for treating cancer containing an agent capable of inhibiting expression of SULF2 (sulfatase 2).

In accordance with another aspect of the present invention, there is provided a method of treating cancer including administering a composition containing an agent capable of inhibiting expression of SULF2 (sulfatase 2).

In accordance with another aspect of the present invention, there is provided the use of a composition containing an agent capable of inhibiting expression of SULF2 (sulfatase 2) for the treatment of cancer.

DESCRIPTION OF DRAWINGS

FIG. 3C shows the expression level of LCN2 mRNA measured by qRT-PCR after treatment with 2 μM sorafenib for 72 hours, and FIG. 3D shows the cell viability of SULF2-WT cells expressing LCN2 shRNA (#252 and #459) after treatment with 0.07813-20 μM sorafenib for 48 hours;

BEST MODE

Unless defined otherwise, all technical and scientific terms used herein have the same meanings as appreciated by those skilled in the field to which the present invention pertains. In general, the nomenclature used herein is well-known in the art and is ordinarily used.

Figure 10:
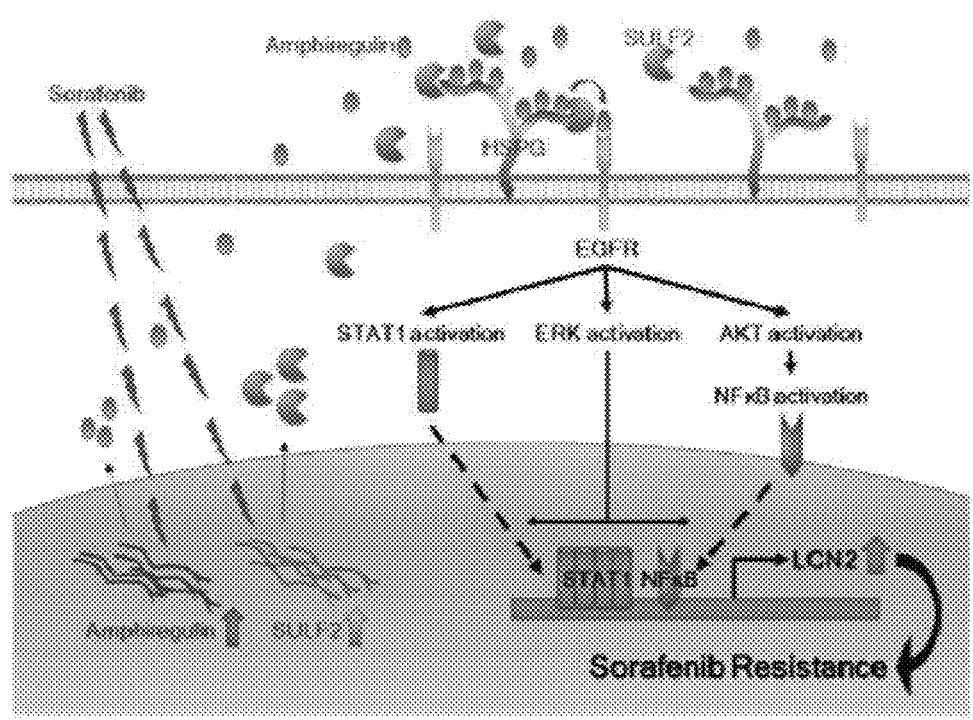
FIG. 10 is a schematic diagram showing SULF2-mediated sorafenib susceptibility control.

Changes in gene functions due to mutations play an important role in the development and progression of cancer (Stratton M R et al., Nature 458: 719-724, 2009). Thus, systematic analysis of drug genomic data identifies viable mutations and new candidates for target drugs. The present invention suggests that the SULF2-EGFR-LCN2 pathway plays a key role in susceptibility to sorafenib and resistance of liver cancer cells (FIG. 10).

The present invention applies a strategy for reanalysis of pharmacogenetic data based on the goal of discovering new drug-gene interactions and identifies 14 unknown viable mutations and drugs for treating the same. Further analysis of the interaction between sorafenib and SULF2 (sulfatase 2) mutations, among a plurality of drug-mutation interaction candidates including sorafenib-SULF2, sorafenib-NTRK3, LBW242-SHC1 and AEW541-ERC1, was performed. The result of further investigation of downstream signals of the SULF2 mutation revealed that LCN2 plays a key role in sorafenib susceptibility through down-regulation of the EGFR signal. That is, the SULF2 mutation (N491K) affects susceptibility to sorafenib and resistance of liver cancer cells, and this effect can be obtained through the deregulation of EGFR and LCN2, and failure to confine the SULF2 mutation to the cell surface results in impairment of binding between the EGFR ligand to EGFR and thus inhibition of downstream EGFR signaling. In addition, sorafenib resistance was found to be reduced through inhibition of the expression of SULF2 or LCN2.

SULF2 is an endosulfatase that catalyzes the selective removal of the 6-O-sulfate group from the internal S-domain of the cell surface and extracellular matrix HS, and is an important regulator of major functions of polysaccharides such as embryogenesis and tissue regeneration in physiological processes (Vines R R et al., Front Oncol 3: 331, 2014). SULF2 is an oncogene that acts through activated receptor tyrosine kinase and downstream MAPK and AKT pathways or Wnt signals, and the expression thereof affects bad prognosis of HCC patients (Lai J P et al., Hepatology 47:1211-22, 2008). In addition, the present inventors have identified a novel SULF2-mediated mechanism of sorafenib sensitivity, which is mediated through at least partial expression of LCN2. LCN2 is a member of the lipocalin superfamily and is a protein group that delivers hydrophobic molecules such as retinoids, fatty acids and organic iron chelators (Flower D R et al., Biochem. Biophys. Res. Commun. 180:69-74, 1991; Schlehuber S. et al., Drug Discov. Today 10:23-33, 2005). LCN2 is known to play an important role in cancer and to contribute to penetration, angiogenesis and drug resistance (Leung L et al., PLoS One 7:e46677, 2012; Shiiba M. et al., Int J Oncol 42:1197-204, 2013). LCN2 is expressed in liver cancer at a higher level than adjacent non-tumor liver tissue. The present invention identifies that the action of SULF2 in cancer cells is mediated through the expression of LCN2.

Figure 6:
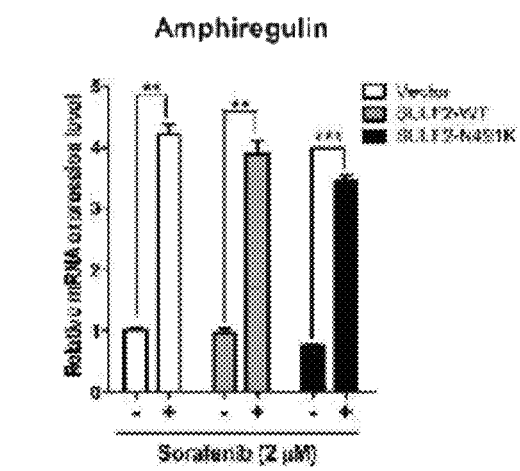
FIG. 6A shows the result of measurement of the mRNA level of amphiregulin through qRT-PCR after treating vector, SULF2-WT and SULF2-N491K cells with 2 μM sorafenib for 72 hours.
FIG. 6B shows protein expression upon treatment with amphiregulin (50 ng/ml)
Figure 6:
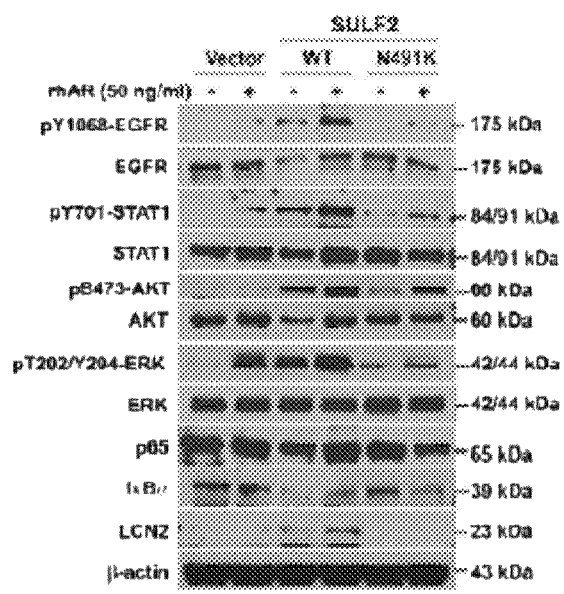
Figure 7:
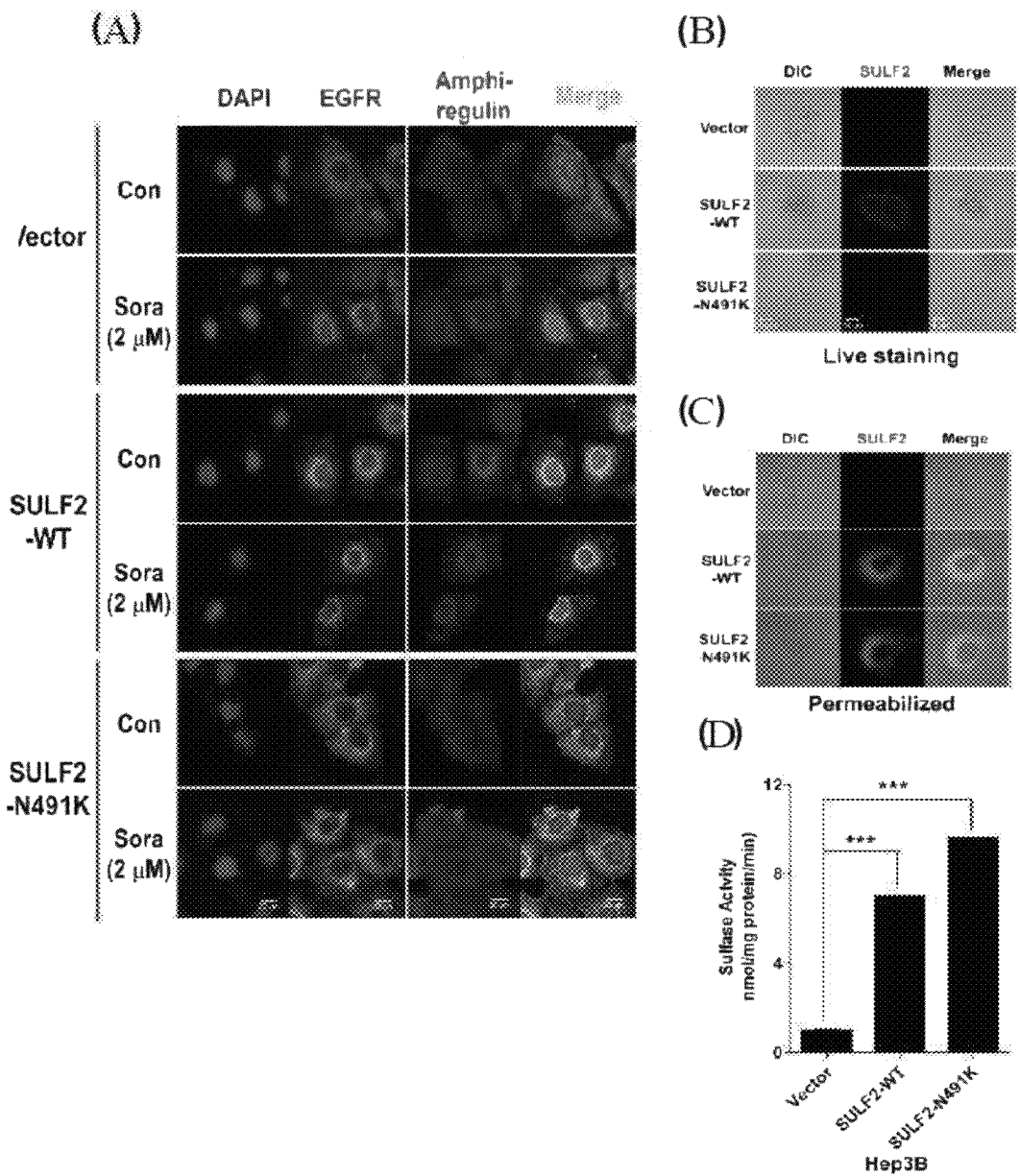
FIG. 7A shows the result of fluorescence staining with EGFR and amphiregulin antibodies after treating vector and SULF2-WT and SULF2-N491K cells with 2 μM sorafenib for 72 hours.
FIG. 7B shows the result of indirect immunofluorescence microscopy of non-permeabilized cells live-stained with SULF2 antibodies.
FIG. 7C shows cells non-permeabilized with 0.2% Triton X-100 and stained with SULF2 antibodies.
FIG. 7D shows the sulfatase activity of the cell lysate after culturing vector, SULF2-WT and SULF2-N491K cells for 24 hours.

It was also identified that induction of LCN2 by SULF2 is mediated by activation of EGFR-dependent signaling pathways including AKT, ERK, STAT1 and NF-κB. It was identified that the activation of EGFR by amphiregulin differs between cells expressing SULF2-WT or SULF2-N491K (FIG. 6B), and that the interaction of EGFR and SULF2 is not regulated by mutation. That is, EGFR has a stronger interaction with SULF2-WT than SULF2-N491K. Moreover, sorafenib treatment significantly increased the interaction between EGFR and SULF2-WT, but did not significantly increase the interaction between EGFR and SULF2-N491K (FIG. 7A). This is because the mutated SULF2 is not confined to the cell surface and thus the binding between the EGFR ligand (such as amphiregulin) and EGFR is impaired (FIG. 7B). In addition, HCC patients treated with sorafenib had an increased amphiregulin serum level.

Meanwhile, analysis of the difference in proliferation and migration between SULF2-WT and SULF2-N491K cells showed that SULF2-WT cells showed rapid proliferation and migration, whereas SULF2-N491K cells showed rapid proliferation, but reduced migration (FIG. 8). This discrepancy can be explained to be due to the difference in FGF and EGF signaling pathways between wild-type and mutant cells. The present invention demonstrated that FGF signals differentially regulated proliferation and migration in SULF2 mutant and wild-type cells (FIGS. 8D and 8E). Similarly, FGF2 stimulates HCC proliferation, activates HCC invasion and stimulates angiogenesis through an autocrine mechanism. FGF2 binding to the receptor FGFR and heparin sulfate proteoglycans (HSPGs) facilitates the formation of complexes essential for cell proliferation and angiogenesis, and sulfatase activation down-regulates FGF signaling through desulfurization of heparan sulfate glycosaminoglycans (HS-GAGs). Accordingly, increased FGF signal caused by inhibition of sulfatase functions in SULF2-N491K cells may contribute to increased proliferative activity. However, unlike the EGFR signal, FGF2 may not improve the migration activity of liver cancer cells.

A variety of signaling pathways including MT-1G, IGF/FGF, Mapk14 (p38a) and CYP3A4 (Tovar V et al., Gut 2015; Rudalska R et al., Nat Med 20:1138-46, 2014; Kuczynski E A et al., Cancer Res 75:2510-9, 2015) are known to induce sorafenib resistance. In addition, it was identified that cells chronically exposed to sorafenib express amphiregulin and have higher EGFR activity, thus supporting the notion that EGFR signaling has an anti-proliferative effect and thus induces resistance to sorafenib treatment (FIG. 6A). In addition, the present inventors investigated whether or not SULF2 expression is associated with acquisition of sorafenib resistance. As a result, they found that knockdown of SULF2 can inhibit EGFR and LCN2 expression and restore drug susceptibility of sorafenib-resistant cells. These results strongly suggest that sorafenib resistance can be reduced by inhibiting the SULF2-EGFR-LCN2 pathway.

In fact, frequent variations of SULF2 including mutations and DNA copy number amplification are actually observed in a variety of types of cancer and SULF2 is known to be overexpressed in about 60% of liver cancer and about 73% of liver cancer cell lines, which is known to be associated with a poor prognosis for patients with liver cancer (Lai J P et al., Hepatology 47: 1211-22, 2008). In addition, sorafenib is the only drug for liver cancer approved by the FDA, but is not routinely recommended by clinicians because the estimated survival benefit is not great compared with the high cost. Therefore, the selection of patients who are susceptible to sorafenib can be of great clinical benefit.

Since a plurality of patients were identified as being subjects who do not respond to the administration and treatment of sorafenib, there was neither method of predicting therapeutic response prior to beginning of treatment, nor method of identifying the same. In addition, there was a problem in that administration of appropriate drugs through prediction of the responsiveness of subjects to treatment with sorafenib was considerably difficult due to insufficient study on reliable genomic biomarkers therefor. Further, there is a problem in that, to date, there is no satisfactory practical research on methods for predicting the responsiveness of patients to treatment with sorafenib by administering an appropriate amount of sorafenib to a plurality of liver cancer patients in order to accomplish the optimal therapeutic effect, alleviate the discomfort of the patients and reduce treatment costs.

In an attempt to solve the above-mentioned problems, a preferred embodiment of the present invention provides a method of predicting the responsiveness to sorafenib treatment by collecting a sample from a subject and analyzing the expression of SULF2 (NCBI GI: 240255476) or LCN2 (NCBI GI: 930697465) gene affecting the responsiveness of sorafenib treatment or a mutation of the gene.

In one aspect, the present invention is directed to a method of predicting susceptibility to sorafenib treatment including (a) extracting DNA or protein from a sample isolated from a subject, (b) measuring an expression level of mRNA of a SULF2 (sulfatase 2) gene or a protein encoded by the gene, and (c) predicting that susceptibility to sorafenib treatment will be high when the expression level is reduced compared to a control group.

In the present invention, the step (b) may further include identifying a mutant of SULF2. Preferably, the mutant is SULF2-N491K in which Asn, the amino acid at position 491 of SULF2, is substituted with Lys, but is not limited thereto.

In the present invention, the subject may be a patient with cancer in need of administration of sorafenib. The cancer is preferably selected from the group consisting of liver cancer, breast cancer, lung cancer, ovarian cancer, pancreatic cancer, skin cancer, a brain tumor, a myeloid tumor and lymphoma, but is not limited thereto. That is, it will be obvious to those skilled in the art that the present invention is applicable to any disease to which sorafenib treatment can be applied.

In the present invention, the sample may be selected from the group consisting of tissues, cells, blood, serum, plasma, saliva, cerebrospinal fluid, sweat, urine, ascites fluid and peritoneal fluid.

In another aspect, the present invention is directed to a composition for predicting susceptibility to sorafenib treatment of a cancer patient containing an agent capable of measuring an expression level of mRNA of a SULF2 (sulfatase 2) gene or a protein encoded by the gene.

In the present invention, the agent capable of measuring the expression level of mRNA is preferably a primer capable of amplifying the SULF2 gene or a probe specifically binding to the SULF2 gene, but is not limited thereto.

The composition may further include an amplification means capable of amplifying the DNA of the sample, and may also optionally include a means for extracting genes from a specimen. Methods for amplifying DNA of the sample using PCR and methods for extracting genes from the specimen are well known in the art and thus a detailed description thereof will be omitted herein.

As used herein, the term "primer" refers to a short nucleic acid sequence having a short free 3-terminal hydroxyl group which can form a base pair with a complementary template and function as a starting point for copying a template strand. Primers can initiate DNA synthesis in the presence of reagents for polymerization reactions (i.e., DNA polymerase or reverse transcriptase) and four different nucleoside triphosphates under conditions of appropriate buffer solutions and temperatures. The PCR conditions and the lengths of the sense and antisense primers can be modified based on those well-known in the art.

As used herein, the term "probe" means a nucleic acid fragment such as RNA or DNA corresponding to several nucleotides to several hundreds of nucleotides capable of specifically binding to mRNA, and is labeled to identify the presence or absence of a specific mRNA.

The probe may be produced in the form of an oligonucleotide probe, a single-stranded DNA probe, a double-stranded DNA probe or an RNA probe. Selection of suitable probes and hybridization conditions can be modified based on those well-known in the art.

The primer or probe of the present invention can be chemically synthesized using a phosphoramidite solid support method or other well-known methods. Such a nucleic acid sequence may also be modified using many means well-known in the art. Non-limiting examples of such modifications include, but are not limited to, methylation, capping, substitution of one or more natural nucleotides with one or more homologues, and modifications between nucleotides, such as modifications into uncharged linkers (e.g., methylphosphonate, phosphotriester, phosphoramidate, carbamate and the like) or charged linkers (e.g., phosphorothioate, phosphorodithioate and the like).

In the present invention, the agent capable of measuring the expression level of protein is preferably an antibody or aptamer specific to the protein encoded by the SULF2 gene, but is not limited thereto.

Examples of a qualitative or quantitative detection/measurement method at a protein level that can be used in the present invention include Western blotting, ELISA, radioimmunoassay, immunodiffusion, immunoelectrophoresis, tissue immunostaining, immunoprecipitation assay, complement fixation assay, binding to labeled antibodies in solution/suspension, mass spectrometry or protein arrays using antibodies Binding with an antibody labeled in a suspension, mass spectrometry or protein array using an antibody.

Reagents or substances used in such methods are well known in the art, and, for example, may be antibodies, substrates, nucleic acid or peptide aptamers that specifically bind to the markers, or receptors or ligands or cofactors that specifically interact with the markers, and may include antibodies, antibody fragments, aptamers, avidity multimers or peptidomimetics capable of specifically binding to a protein.

The SULF2 or LCN2 protein detection of the present invention is based on a method for detecting a complex of a SALF2 or LCN2 protein with a DNA aptamer that specifically binds to the SULF2 or LCN2 protein. In order to facilitate detection of the complex, the DNA aptamer that specifically binds to the SULF2 or LCN2 protein of the present invention may include a fluorescent material, such as fluorescein Cy3 or Cy5, or a radioactive substance or a chemical substance, for example, a nucleotide labeled with biotin or modified with a primary amine.

The DNA aptamer that specifically binds to the SULF2 or LCN2 protein of the present invention can, for example, be biotinylated, which can be successfully fixed on streptavidin-coated wells. The DNA aptamer that specifically binds to the SULF2 or LCN2 protein of the present invention fixed on the wells may be bound with a SULF2 or LCN2 protein, and the SULF2 or LCN2 protein bound to the DNA aptamer fixed on the wells can be used to visualize the capture using a DNA aptamer specifically binding to the SULF2 or LCN2 protein again.

In another aspect, the present invention is directed to a composition for predicting susceptibility to sorafenib treatment of a cancer patient containing an agent capable of detecting a SULF2 (sulfatase 2) mutant.

In the present invention, the mutant is preferably SULF2-N491K, in which Asn, which is an amino acid at position 491 of SULF2, is substituted with Lys, but is not limited thereto.

In the present invention, the agent capable of detecting the mutant is selected from the group consisting of a primer capable of amplifying a SULF2-N491K gene, a probe specifically binding to the SULF2-N491K gene, and an antibody or aptamer specific to a SULF2-N491K protein.

In the present invention, the cancer is preferably selected from the group consisting of liver cancer, breast cancer, lung cancer, ovarian cancer, pancreatic cancer, skin cancer, a brain tumor, a myeloid tumor and lymphoma, but is not limited thereto.

As herein used, the term "prediction" relates to the possibility and/or likelihood of survival of a patient who preferentially or non-preferentially responds to treatment such as chemotherapy, when receiving any treatment, for example, by administration of a particular therapeutic agent and/or removal of a primary tumor through surgery, and/or chemotherapy for a particular period of time without recurrence. The prediction method of the present invention can be used clinically to make treatment decisions by selecting the optimal treatment approach for liver cancer patients. The prediction method of the present invention may also be used to determine whether or not a patient is preferentially responsive to treatment regimens including administration of a predetermined therapeutic agent or a combination thereof, surgical intervention, chemotherapy or the like, or to predict whether or not long-term survival of a patient is possible.

In another aspect, the present invention is directed to a pharmaceutical composition for treating cancer containing an agent capable of inhibiting expression of SULF2 (sulfatase 2).

In another aspect, the present invention is directed to a method of treating cancer including administering a composition containing an agent capable of inhibiting expression of SULF2 (sulfatase 2).

In another aspect, the present invention is directed to the use of a composition containing an agent capable of inhibiting expression of SULF2 (sulfatase 2) for the treatment of cancer.

In the present invention, the cancer is cancer resistant to sorafenib, and the cancer is preferably selected from the group consisting of liver cancer, breast cancer, lung cancer, ovarian cancer, pancreatic cancer, skin cancer, a brain tumor, a myeloid tumor and lymphoma, but is not limited thereto.

In the present invention, the agent capable of inhibiting the expression of SULF2 is preferably selected from the group consisting of siRNA, antibodies, aptamers or small-molecule compounds specific to SULF2, but is not limited thereto.

As used herein, the term "agent capable of inhibiting expression" means a substance capable of inhibiting the production of a transcript or protein expressed and produced in a gene. Examples of the agent include transcription factors that bind to genes and inhibit at a transcription level, interfering RNAs such as miRNA, siRNA and shRNA that bind to the transcribed and synthesized transcript and degrade the transcript, antibodies capable of binding to the expressed SULF2 or LCN2 protein, and the like.

As herein used, the term "short interfering RNA" means a double-stranded RNA capable of inducing RNAi which inhibits the activity of a gene. In the present invention, the interfering RNA may be miRNA, siRNA, shRNA, or the like capable of inhibiting the expression of SULF2 or LCN2. The interfering RNA may be any form of inducing mRNA of SULF2 or LCN2, for example, siRNA obtained by chemical synthesis, biochemical synthesis or in-vivo synthesis, or double-stranded RNA of 10 base pairs or more, in which double-stranded RNA of about 40 bases or more is degraded in vivo, can be used.

The interfering RNA may have a homology, with a part of a nucleic acid sequence of SULF2 or LCN2 RNA, of least about 70%, preferably at least 75%, more preferably at least 80%, even more preferably at least 85%, even more preferably at least 90%, particularly preferably at least 95%, and most preferably 100%. The RNA including the double-stranded portion or a variant thereof may be used. The sequence part having a homology is usually at least 15 nucleotides, preferably at least about 19 nucleotides, more preferably at least 20 nucleotides, and even more preferably at least 21 nucleotides.

As herein used, the term "antibody" means a proteinaceous molecule capable of specifically binding to an antigenic site of a protein or peptide molecule. Such an antibody can be prepared through a conventional method from a protein obtained by cloning the corresponding gene into an expression vector in accordance with a conventional method. There is no particular limitation as to the form of the antibody, and the antibody according to the present invention may include a polyclonal antibody, a monoclonal antibody or a fragment of an antibody that has an antigen-binding property, and may include all immunoglobulin antibodies and specific antibodies such as humanized antibodies. In addition, the antibody includes not only a complete antibody having two full-length light chains and two full-length heavy chains, but also a functional fragment of an antibody molecule. The term "functional fragment of antibody molecule" means a fragment having at least an antigen-binding function, and may be Fab, F(ab'), F(ab')$_2$, Fv or the like.

In the present invention, the antibody may be an antibody capable of specifically binding to a SULF2 or LCN2 protein, preferably a polyclonal antibody, a monoclonal antibody or a fragment thereof capable of specifically binding to a SULF2 or LCN2 protein.

As herein used, the term "resistant cancer" means cancer which has extremely low susceptibility to chemotherapy or radiation therapy and symptoms of which are not improved, alleviated, relieved or treated by the above-mentioned therapy. The resistant cancer may be resistant to certain anticancer agents or radiation therapies at the onset, or may not exhibit resistance at the onset, but have no further susceptibility to the same therapeutic agent due to mutations of genes in the cancer cells upon long-term treatment.

In the present invention, the resistant cancer may be any cancer that is resistant to radiation therapy or chemotherapy, but is not particularly limited thereto. Specific examples thereof include liver cancer, lung cancer, cervical cancer, colon cancer, breast cancer and the like, which are resistant to radiation therapy or chemotherapy due to the overexpression of SULF2 or LCN2.

The composition according to the present invention may be used for combination therapy using radiation or an anticancer agent. The anticancer agent may be selected from the group consisting of sorafenib, OKN-007, gefitinib, doxorubicin, vinblastine, taxol, Etoposide, cisplatin, 5-FU, ifosfamide, and combinations thereof, but is not limited thereto.

The pharmaceutical composition for treating cancer resistant to radiation or drugs according to the present invention includes a SULF2 or LCN inhibitor, thereby having an effect of suppressing resistance to radiation or drugs provided by SULF2 or LCN. Thus, cancer resistant to radiation or drugs can be treated by administering the pharmaceutical composition alone to a patient with the cancer that is resistant to radiation or drugs, or administering the pharmaceutical composition of the present invention in combination with a conventional chemotherapeutic agent, which does not exhibit any therapeutic effect due to the resistance caused by SULF2 or LCN. In particular, when the pharmaceutical composition of the present invention is administered in combination with a conventional anticancer agent, the anticancer activity provided by the conventional anticancer agent and the anticancer activity provided by the pharmaceutical composition of the present invention act with each other synergistically, thereby treating cancer more effectively. Conventional anticancer agents that can be used herein are not particularly limited as long as they are resistant to SULF2 or LCN, but are preferably sorafenib, OKN-007, gefitinib or a combination thereof.

The pharmaceutical composition of the present invention may further include a suitable carrier, excipient or diluent conventionally used in the preparation of pharmaceutical compositions. Specifically, the pharmaceutical composition may be formulated in the form of an oral formulation such as a powder, granule, tablet, capsule, suspension, emulsion, syrup or aerosol, an external preparation, a suppository and a sterilized injection solution according to a conventional method. In the present invention, the carrier, excipient or diluent which may be contained in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. In the case of formulation, a typically used diluent or excipient, such as a filler, an extender, a binder, a wetting agent, a disintegrant or a surfactant, is used. Solid formulations for oral administration may be tablets, pills, powders, granules, capsules and the like, which may be prepared by mixing at least one excipient, for example, starch, calcium carbonate, sucrose, lactose, gelatin or the like. In addition to simple excipients, lubricants such as magnesium stearate and talc are also used. Liquid formulations for oral administration may be suspensions, oral liquids and solutions, emulsions, syrups and the like, and may include various excipients such as wetting agents, sweeteners, fragrances, preservatives and the like, in addition to water and liquid paraffin, which are simple diluents that are commonly used. Formulations for parenteral administration may be sterilized aqueous solutions, non-aqueous solutions, suspensions, emulsions, freeze-dried preparations and suppositories. Examples of the non-aqueous solutions and suspensions include propylene glycol, polyethylene glycol, vegetable oil such as olive oil, injectable ester such as ethyl oleate, and the like. Examples of the suppository base include Witepsol, macrogol, Tween 61, cacao butter, laurin butter, glycerogelatin and the like.

The content of the agent in the pharmaceutical composition according to an embodiment of the present invention is not particularly limited, but may be within the range of 0.0001 to 50% by weight, more preferably 0.01 to 10% by weight, based on the total weight of the final composition.

The pharmaceutical composition of the present invention is administered in a pharmaceutically effective amount. As used herein, the term "pharmaceutically effective amount" refers to an amount of a pharmaceutical composition which is sufficient to treat or prevent diseases at a reasonable benefit/risk ratio applicable to all medical treatments or preventions. The effective amount level may be changed depending on a variety of factors including severity of disease, activity of the drug, the age, body weight, state of health and gender of the patient, sensitivity of the patient to the drug, administration time, administration route, excretion rate and treatment period of the composition according to the present invention, and drugs mixed with or used in combination with the composition according to the present invention, and other factors well-known in the art. The pharmaceutical composition of the present invention may be administered alone or in combination with other therapeutics. In this case, the pharmaceutical composition of the present invention may be administered sequentially or simultaneously with conventional therapeutics. In addition, the pharmaceutical composition may be administered once or several times. It is important to administer the minimal amount sufficient to achieve the maximum efficacy without side effects, while thoroughly taking into consideration these factors.

The dosage of the pharmaceutical composition of the present invention can be determined by those skilled in the art in consideration of a variety of factors including use purpose, severity of disease, age, body weight and gender of the patient, anamnesis and the type of substance used as an active ingredient. For example, the pharmaceutical composition may be administered in a dose of 10 to 100 mg/kg, more preferably, 10 to 30 mg/kg daily to mammals, and the administration frequency of the composition according to the present invention may be one to three times a day, or several times in several divided doses, but is not particularly limited thereto.

As herein used, the term "subject" or "object" means all animals including humans afflicted with resistant cancer. By administering the composition of the present invention to a subject, resistant cancer can be treated.

As herein used, the term "treatment or therapy" means any action that alleviates or positively alters cancer resistant to radiation or drugs by administering the pharmaceutical composition of the present invention.

As used herein, the term "administration" refers to an action of introducing the pharmaceutical composition according to the present invention into a subject by any appropriate method, and the route of administration may be any route such as oral or parenteral route, so long as it enables the composition to be delivered to a target tissue.

The pharmaceutical composition can be administered via any general route that enables the composition to be delivered to a target tissue. The pharmaceutical composition is not particularly limited, and may be administered intraperitonealy, intravenously, intramuscularly, subcutaneously, intradermally, orally, intranasally, intrapulmonarily or rectally. In addition, the composition may be administered by any device capable of delivering the active agent to the target cell.

Example

Hereinafter, the present invention will be described in more detail with reference to examples. However, it will be obvious to those skilled in the art that these examples are provided only for illustration of the present invention and should not be construed as limiting the scope of the present invention based on the subject matter of the present invention.

Cells, Antibodies and Reagents

Human liver cancer cells of Hep3B, Huh7, HepG2 and PLC/PRF5 were cultured in DMEM supplemented with 10% FBS, 100 U/ml penicillin and 100 µg/ml streptomycin.

SULF2 antibodies were purchased from Novus Biologicals and EGFR, p-EGFR (Tyr1068), ERK (1/2), p-ERK (1/2), AKT, p-AKT, STAT1, p-STAT1 (Tyr701), STAT3, p-STAT3 (Tyr705), IκBα, LCN2, p-FGFR (Tyr653/654), FGFR and actin antibodies were purchased from Cell Signaling Biotechnology (Danvers, Mass., USA), and amphiregulin, p65 and U-0126 antibodies were purchased from Santa Cruz Biotechnology (Dallas, Tex., USA).

Sorafenib was purchased from LC Laboratories (Woburn, Mass., USA), recombinant human amphiregulin was purchased from R & D systems (Minneapolis, Minn., USA), AEW541 was purchased from AdoQ bioscience (Burlington, Canada), gefitinib and PD173074 were purchased from Tocris Bioscience (Bristol, UK), and OKN-007 and LBW242 were purchased from MedKoo Biosciences (Chapel Hill, N.C., USA).

Expression Constructs and Lentiviral Vector Transfection

A lentiviral construct expressing STAT1 shRNA, p65 shRNA and LCN2 shRNA was purchased from Sigma-Aldrich. Wild-type SULF2, SULF2-N491K, wild-type ERC1, ERC1-H721Q, wild-type NTRK3, NTRK3-N522K, wild-type SHC1 and SHC1-SHC1-P55 cDNA constructs were cloned into MCS-EF1-Puro (System Biosciences, Mountain), the lentiviral vectors for cDNA expression. All lentiviral vectors were transfected into 293 TN cells (System Biosciences) using the Lipofectamine 3000 transfection reagent (Invitrogen, Waltham, Mass., USA). Two days after lentiviral plasmid transfection, particles were collected and used to infect HCC cells. The HDD cells infected with lentivirus were selected using puromycin for 1 week.

Example 1: Identification of Drug-Mutation Interactions 1-1: Drug Susceptibility Mutation Candidate CCLE data were evaluated to identify specific changes in drug susceptibility mutations. Mutation and drug susceptibility data for CCLE were obtained from broadinstitue.org/ccle.

First, data of seven tissue types including breast, central nervous system, hematopoietic and lymphoid tumors, lung, ovary, pancreas and skin tumors were selected, each of which was presented through at least 25 cell lines. The selected data consisted of 290 cell lines and 33,444 sequence variants. Depending on the characteristics of the mutation, loss-of-function mutation (LOF) including nonsense, frameshift insertions or deletions and splice sites was classified as "mutLOF", the missense mutation was classified as "nnMS", and the mutation having a combination of characteristics of mutLOF and nnMS was classified as "mutLOF+nnMS" (Barretina J et al., Nature 483: 603-7, 2012).

The mutations were observed as mutLOF (n=1,907), mutLOF+nnMS (n=3,472) and nnMS (n=1,565).

Figure 1:
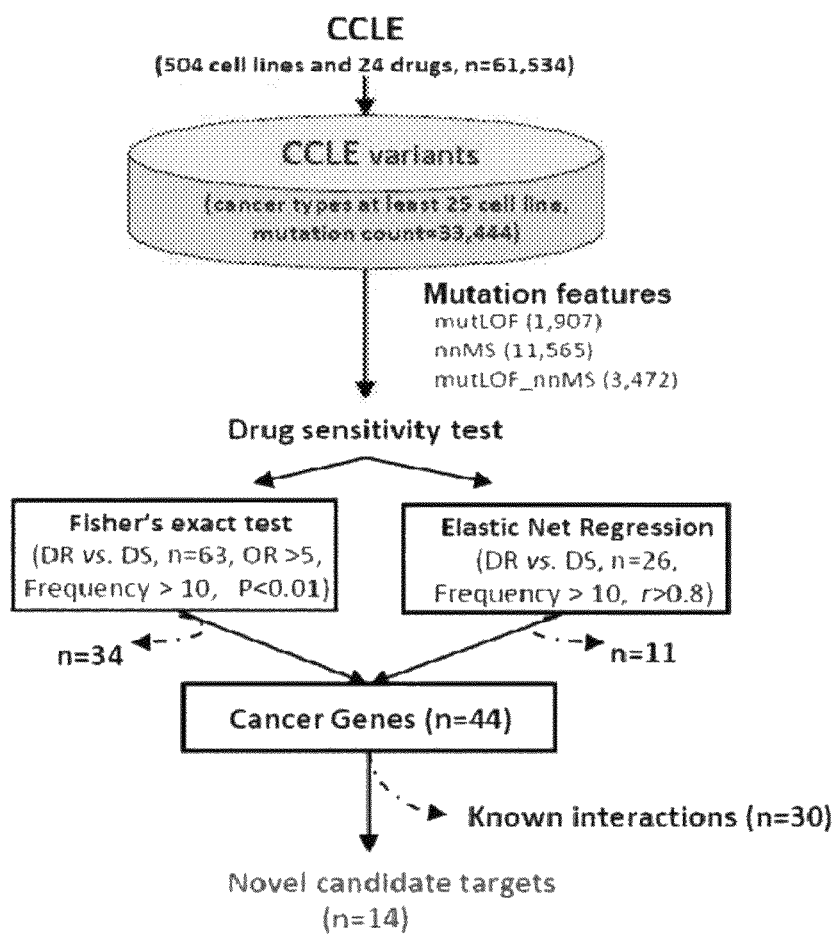
FIG. 1 is a flowchart for identifying a drug-susceptible mutant gene.
Figure 2:
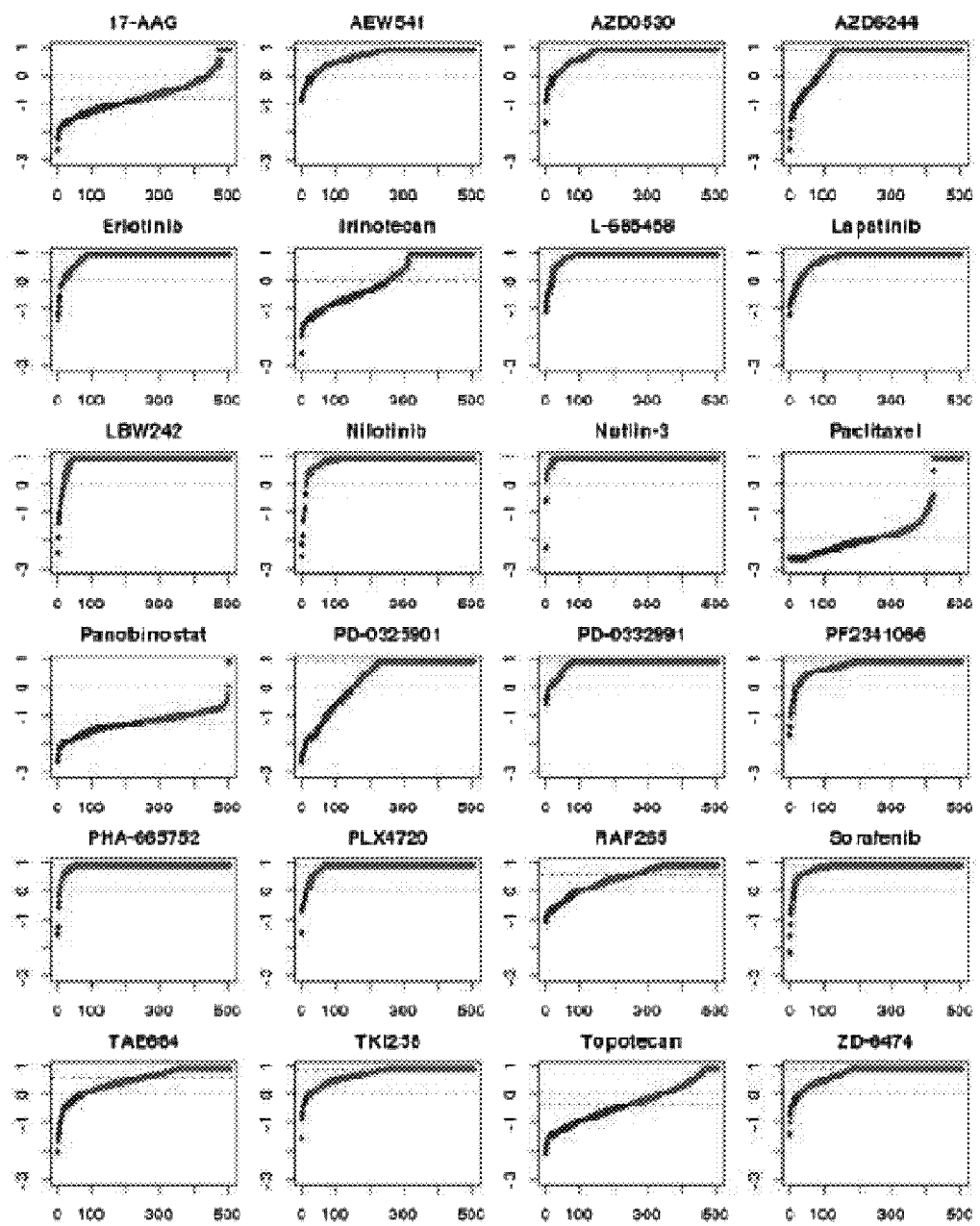
FIG. 2 shows the classification of susceptibility of cell lines to 24 anti-cancer drugs, wherein sensitive and resistant cell lines are classified depending on the median value of log 10 ($IC_{50}$)

Subsequently, the drug susceptibility of mutations was evaluated using Fisher's exact test and elastic net regression (FIG. 1).

Cell lines were classified into two groups, namely resistant (R) and sensitive (S) groups, based on the median value of log-transformed $IC_{50}$ of each drug, and the association between drug sensitivity group and drug sensitivity was estimated by elastic net regression and Fishers exact T-test. In other words, elastic net regression was performed using the R package library glmnet (Barretina J et al., Nature 483: 603-7, 2012), parameter optimization for α and λ was estimated through rounds of leave-group-out cross validation, and the importance of drug mutation interaction was determined by performing a bootstrapping procedure 200 times. In addition, Fisher's exact test was performed, and the significance was determined based on an odds ratio (OR)>5 and P<0.01.

TABLE 1

A systemic screen for drug associated mutations identified drug-related novel target gene

| Feature Type | Drug | Predicted Target | CCLE/PubChem Target | Frequency | Odds Ratio/ EN coef* | Lower 95% CI | Upper 95% CI | P-value/r** | Analysis Type |
|---|---|---|---|---|---|---|---|---|---|
| mutLOF_nnMS | A200530 | RBBP8 | ABL/SRC, ABL1 | 11 | 11.24 | 2.24 | 48.52 | 0.002/ 0.03 | Fisher |
| nnMS | Sorafenib | SULF2 | RTK/PDGFR, KDR, KIT, FLT3 | 15 | 11.10 | 1.72 | 52.70 | 0.006 | Fisher |
| mutLOF_nnMS | Sorafenib | SULF2 | RTK/PDGFR, KDR, KIT, FLT3 | 16 | 10.74 | 1.68 | 50.29 | 0.007 | Fisher |
| mutLOF_nnMS | LBW242 | GUCY1A2 | XIAP/IAP | 11 | 10.45 | 1.63 | 49.53 | 0.007 | Fisher |
| mutLOF_nnMS | LBW242 | SHC1 | XIAP/IAP | 11 | 10.45 | 1.63 | 49.53 | 0.007 | Fisher |
| mutLOF_nnMS | Sorafenib | NTRK3 | RTK/PDGFR, KDR, KIT, FLT3 | 17 | 9.96 | 1.57 | 46.12 | 0.008 | Fisher |
| nnMS | Sorafenib | NTRK3 | RTK/PDGFR, KDR, KIT, FLT3 | 17 | 9.49 | 1.49 | 43.95 | 0.009 | Fisher |
| mutLOF_nnMS | AEW541 | ERC1 | IGF1R | 12 | 7.25 | 1.51 | 29.15 | 0.007 | Fisher |
| nnMS | PLXA720 | NIN | RAF/BRAF | 23 | 6.74 | 1.45 | 25.15 | 0.008 | Fisher |
| mutLOF_nnMS | PD-0325901 | RBBP8 | MEK/MEK1, MEK2 | 11 | 6.40 | 1.51 | 38.04 | 0.004 | Fisher |
| nnMS | AEW541 | PTPRD | IGF1R | 23 | 5.37 | 1.59 | 15.94 | 0.004 | Fisher |
| mutLOF_nnMS | AEW541 | PTPRD | IGF1R | 28 | 5.26 | 1.72 | 14.46 | 0.002 | Fisher |
| mutLOF | Topotocan | EP300 | TOP1 | 14 | 3.18* | — | — | 0.99* | EN |
| mutLOF | Topotocan | PDE4DIP | TOP1 | 195 | 0.62* | — | — | 0.88* | EN |

For regularized elastic net regression analysis, the significant bootstrap datasets with the elastic net regression coefficients greater than 0 were determined. And the average coefficients* from the significant Bootstrap datasets and the percentage of significant bootstrap datasets** from all the bootstrap data sets are indicated.

As a result, it was possible to select mutations with increased drug sensitivity, and 89 drug-mutation pairs were identified as potential candidates for drug-mutation interactions. Among them, the genes (n=41) known to interact with the drugs listed in the PubChem database (pubchem.ncbi.nlm.nih.gov/) were filtered. Then, cancer-associated genes (n=44) were selected using information from a publicly available website (bushmanlab.org/links/genelists, allOnco, n=2,125) In addition, known drug-gene interactions (n=30) were identified by searching the PubMed literature and filtered. Finally, 14 pairs of drug-mutation candidates suspected of having altered drug sensitivity through mutation were determined (Table 1).

1-2: Testing

Four drug-mutation interactions were assessed by examining specific variants for drug sensitivity of the candidates. The RBBP8 mutation showed the most significant association (p=0.002) with the AZD0530 drug, but drug-mutation interactions of SULF2-N491K, SHC1-P5S, NTRK3-N522K and ERC1-H721Q mutations were evaluated, since it was difficult to produce the RBBP8 mutation.

As a result, in SHC1-P5S mutation, Huh7 cells were sensitized by LBW242 as compared to cells expressing SHC1-WT (SHC1-WT: $IC_{50}$=4.260 and SHC1-P5S: $IC_{50}$=2.256). In addition, the result of identification as to whether or not NTRK3-N522K mutation affects sorafenib sensitivity showed that Huh7 cells expressing the NTRK3-N522K mutation had lower $IC_{50}$ values for sorafenib than wild-type NTRK3-WT cells (NTRK3-WT: $IC_{50}$=7.64 μM and NTRK3-N522K: $IC_{50}$=5.80 μM). Similarly, the ERC1-H721Q mutation sensitized HepG2 cells by AEW541 (ERC1-WT: $IC_{50}$=4.25 μM and ERC1-H721Q: $IC_{50}$=2.63 μM).

These analysis results suggest that analytical strategies for identifying new drug-mutation interactions are appropriate and reliable.

Example 2: Increased Susceptibility to Sorafenib in Liver Cancer Cells by SULF2 Mutation SULF2 mutations showed significant changes in sorafenib susceptibility (Table 1). Cells with a SULF2 mutation having the features of nMS (p=0.006, odds ratio [OR]=11.10) and mutLOF+nnMS (p=0.007, OR=10.74) were significantly sensitized to sorafenib treatment. Thus, in the following examples, the molecular mechanisms and signaling pathways involved in the mutation were analyzed (FIG. 1). In particular, molecular mechanisms underlying interactions between sorafenib and SULF2 mutations in liver cancer were further investigated. SULF2 was expressed in several liver cancer cell lines, and the Huh7 and HepG2 cells, which most strongly expressed SULF2, were selected.

2-1: Overexpression of SULF2 Mutation

Figure 3A:
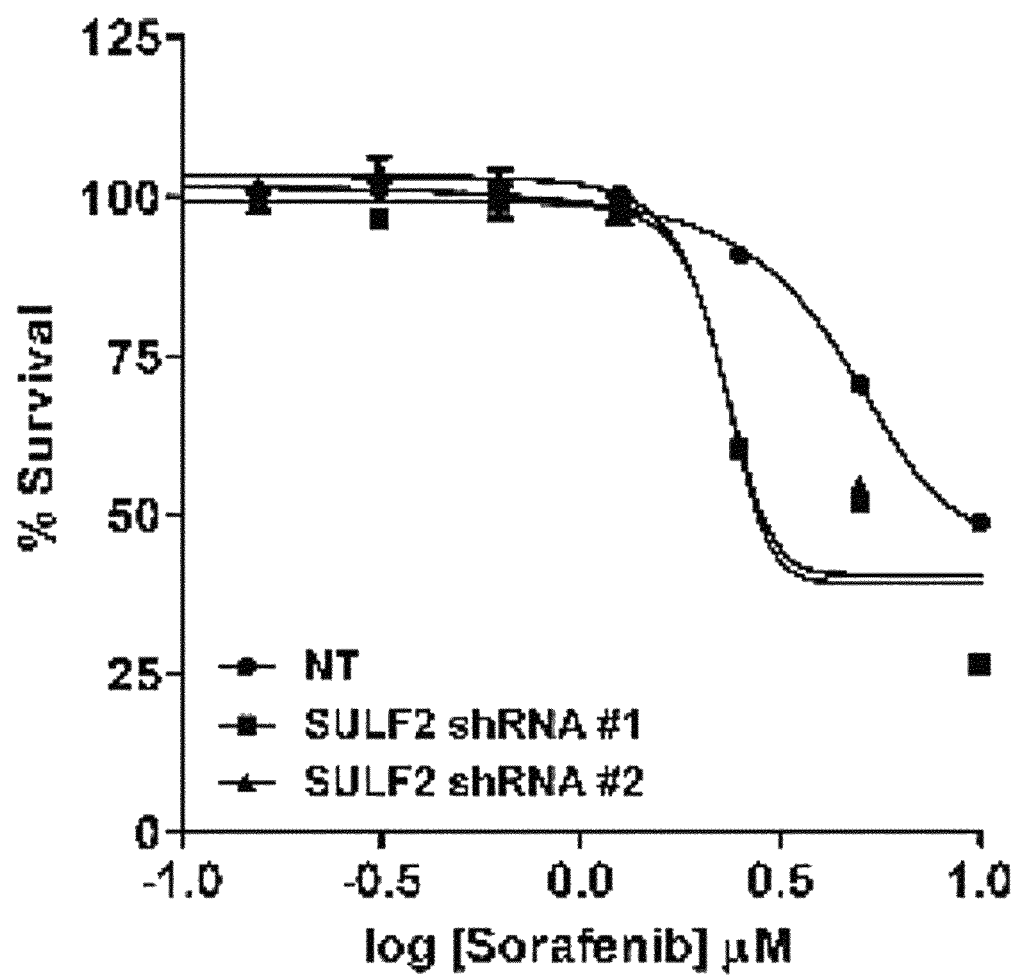
FIG. 3A shows the cell viability of Huh7 cells expressing NT shRNA or SULF2 shRNA (#1 or #2) when treating the Huh7 cells with sorafenib at a concentration of 0.07813-20 μM for 48 hours.
Figure 3B:
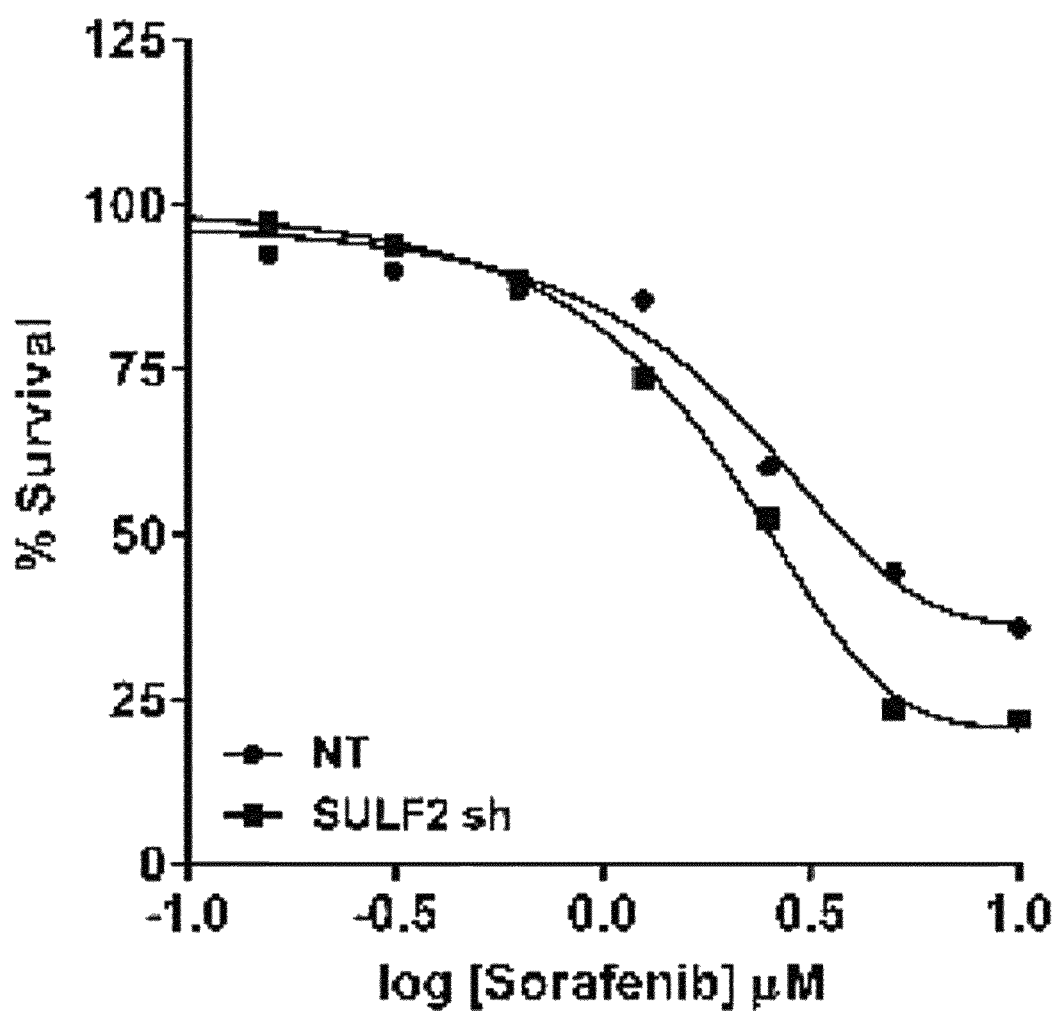
FIG. 3B shows the cell viability of HepG2 cells expressing NT shRNA or SULF2 shRNA.

First, SULF2 was knocked down with shRNA and the knockdown of SULF2 protein was identified through Western blotting. As a result, the $IC_{50}$ values for sorafenib treatment in Huh7 and HepG2 cells were significantly reduced to 6.17 μM and 2.38 μM, respectively, by SULF2 knockdown compared to NT with 10.17 μM and 4.97 μM (FIGS. 3A and 3B).

Then, in order to identify whether or not the SULF2 mutation changed drug susceptibility, an overexpression system for wild-type SULF2 and SULF2-N491K mutants in Hep3B cells that rarely expressed endogenous SULF2 was established (Lai J P et al., Hepatology 47: 1211-22, 2008).

The $IC_{50}$ values of sorafenib in Hep3B cells transfected with the vector, SULF2-WT or SULF2-N491K, were measured through WST-1 assay.

Figure 3C:
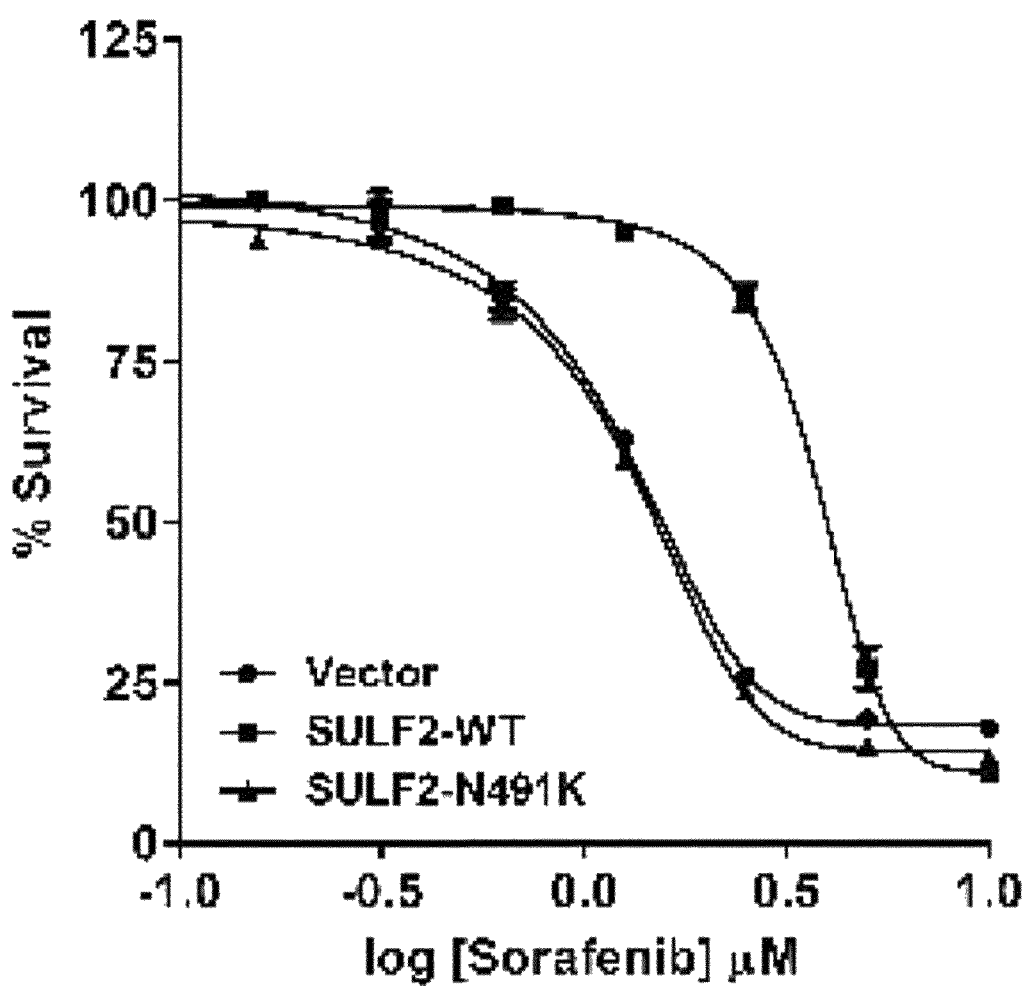
FIG. 3C shows the cell viability of Hep3B cells overexpressing vectors, SULF2-WT and SULF2-N491K.

As a result, Hep3B-SULF2-WT (SULF2-WT) cells showed an $IC_{50}$ value of 7.511 μM, which was significantly increased compared to the $IC_{50}$ value of Hep3B-vector cells of 3.372 μM. This means that sorafenib resistance was improved. On the other hand, cells expressing SULF2-N491K (SULF2-N491K) exhibited considerably higher sorafenib sensitivity ($IC_{50}$=3.54 μM) than SULF2-WT cells (FIG. 3C). That is, the susceptibility to sorafenib was increased by SULF2 mutation. These results suggest that the degree of SULF2 expression is closely related to susceptibility to sorafenib in liver cancer cells.

2-2: SULF2 Inhibition

The effect of 2,4-disulfonylphenyl-tert-butylnitrone (OKN-007), a SULF2 inhibitor, on sorafenib susceptibility was evaluated.

Figure 3D:
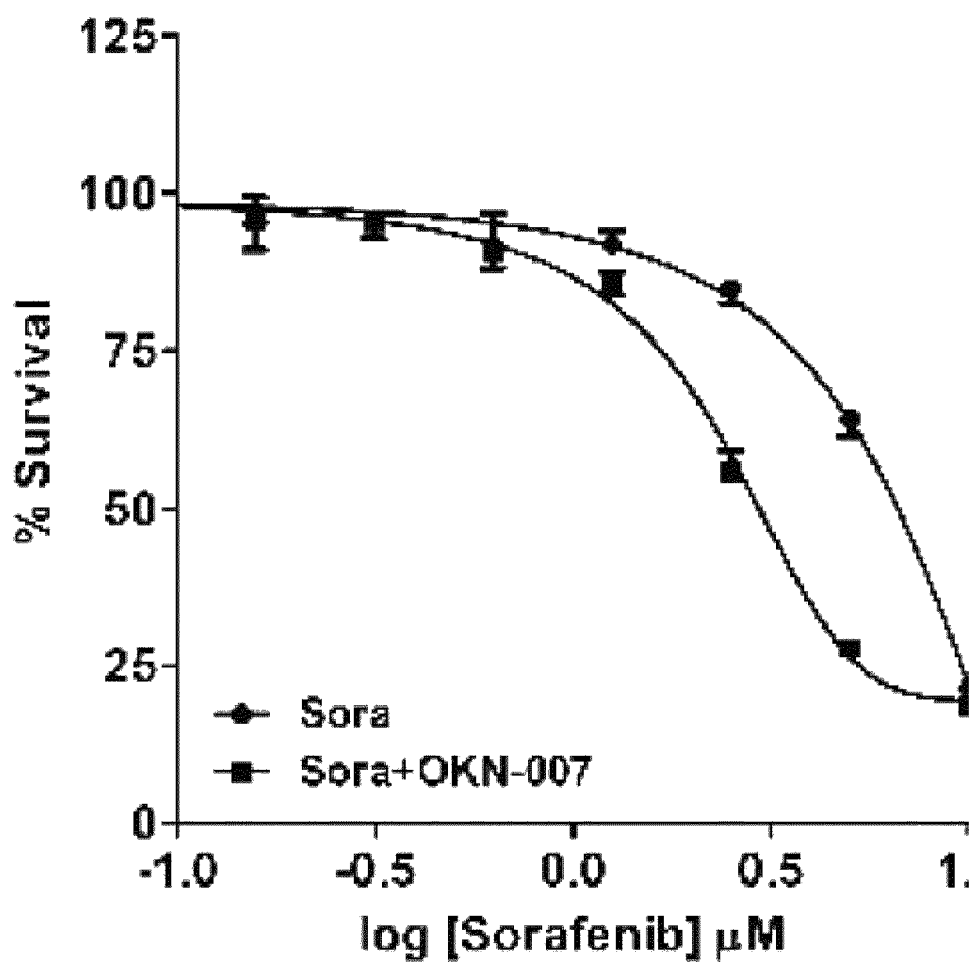
FIG. 3D shows the cell viability of Huh7 cells treated with 0.07813-20 μM sorafenib, or a combination of 200 μM OKN-007 and 0.07813-20 μM sorafenib.
Figure 3E:
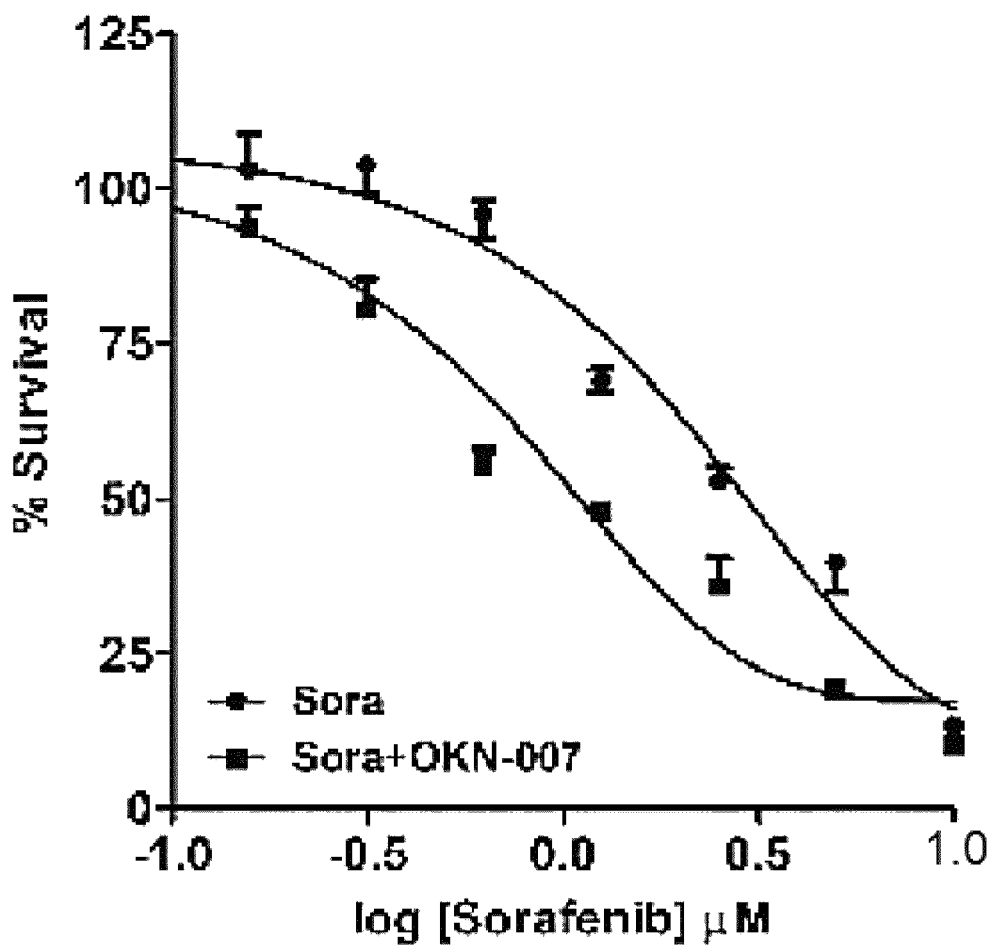
FIG. 3E shows the cell viability of HepG2 cells.
Figure 3F:
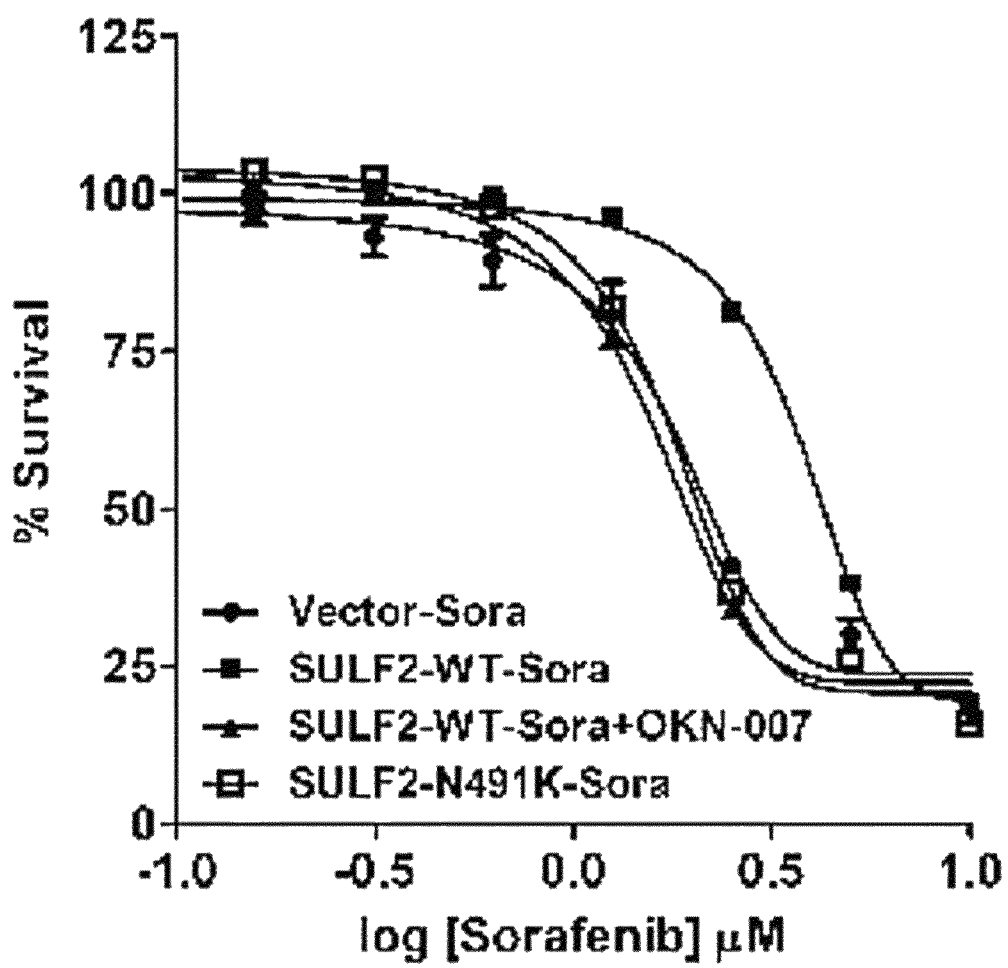
FIG. 3F shows the cell viability of Hep3B cells overexpressing vectors, SULF2-WT and SULF2-N491K when treating the Hep3B cells with sorafenib, or a combination of OKN-007 and sorafenib for 48 hours.

As a result, the susceptibility of sorafenib was increased when treating Huh7, HepG2 and Hep3B, which were several liver cancer cells expressing wild-type SULF2, with OKN-007 (Huh7: $IC_{50}$=5.062 μM, HepG2: $IC_{50}$=1.755 μM, Hep3B: $IC_{50}$=3.169 μM) (FIGS. 3D, 3E and 3F), which were consistent with SULF2 knockdown results. In contrast, susceptibility of vector and SULF2-N491K cells to sorafenib did not change, even with OKN-007 treatment. In conclusion, these results suggest that SULF2 is an important regulator of susceptibility to sorafenib in liver cancer cells.

Example 3: LCN2, Effector Gene of SULF2-Dependent Sorafenib Susceptibility 3-1: Analysis of Gene Expression Between SULF2-WT and SULF2-N491K Cells To identify the effect of SULF2 expression on sorafenib susceptibility, gene expression of Hep3B cells expressing SULF2-WT or SULF2-N491K was analyzed.

The total RNA was extracted according to the manufacturer's instructions (mirVana total RNA extraction kit, Ambion, Austin, Tex.), and cRNA was produced with 500 ng of total RNA per sample using an illumine RNA amplification kit (Ambion). A total of 750 ng of cRNA was used for hybridization to the human HT12-v4 Illumina bead chip gene expression sequence (Illumina). Data normalization was performed using log-2 transformation and quantization/normalization, and data processing and statistical analysis were performed using the R/Bioconductor package.

As a result, differentially expressed genes (DEGs) of 92 up-regulation and 17 down-regulation, which differed by 1.4 times or more between the two cells of SULF2-WT and SULF2-N491K, were identified (FIG. 4A), and LCN2 was identified to be the top up-regulation gene in SULF2-WT cells.

3-2: Analysis of LCN2 Expression in SULF2-WT and SULF2-N491K Cells

Then, the expression of LCN2 was found again in vector, SULF2-WT and SULF2-N491K cells by qRT-PCR.

Figure 4:
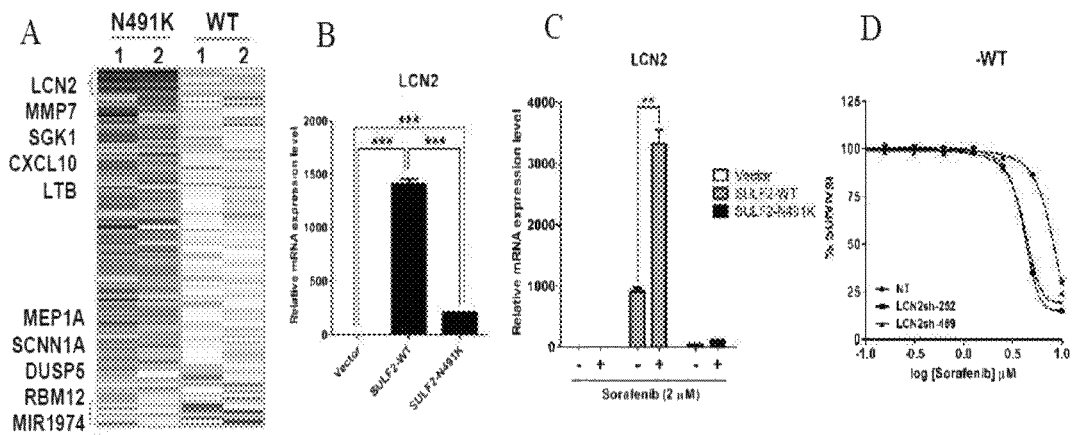
FIG. 4A shows the differential expression of genes between SULF2-WT and SULF2-N491K cells.
FIG. 4B shows the expression levels of LCN2 mRNA in vector, SULF2-WT and SULF2-N491K cells measured by qRT-PCR.

Each cell was collected using an RNeasy kit (Qiagen, Venlo, Netherlands) and total RNA was isolated. The mRNA was reverse-transcribed into cDNA using a PrimeScript RT kit (Takara, Shiga, Japan), and then PCR was conducted using the CFX96 Real-Time PCR Detection System (Bio-Rad Laboratories, Hercules, Calif., USA) equipped with SsoAdvanced Universal Supermixes (Bio-Rad). The sequences of the primers are shown in Table 2 below. The analysis of each sample was run at least three times for each experiment, and the data for the number was reported in a relative quantity: Mean value (standard deviation) of $2^{-\Delta\Delta CT} \pm S.D.$ As a result, LCN2 was overexpressed (>1,400-fold) in SULF2-WT cells and LCN2 expression was reduced (200-fold) in SULF2-N491K cells compared to vector cells (FIG. 4B). Thus, it can be seen that LCN2 is a key effector gene of SULF2-dependent sorafenib susceptibility.

TABLE 2

| Gene | | Primer sequences | SEQ ID NO |
|---|---|---|---|
| SULF2 | Forward | 5'-CATAGAAGATTCT AGAATGGGCCCCCCGA G-3' | 1 |
| | Reverse | 5'-CAGATCCTTGCGG CCGCTCAACCTTCCCA GCCTTCCC-3' | 2 |
| LCN2 | Forward | 5'-CAGCAGAACTTCC AGGACAA-3' | 3 |
| | Reverse | 5'-TAAACAGGACGGA GGTGACA-3' | 4 |
| Amphi-regulin | Forward | 5'-GCTGTCGCTCTTG ATACTCG-3' | 5 |
| | Reverse | 5'-AATCCATCAGCAC TGTGGTC-3' | 6 |
| SHC1 | Forward | 5'-CATAGAAGATTCT AGAATGGATCTCCTGC CCCC-3' | 7 |
| | Reverse | 5'-CAGATCCTTGCGG CCGCTCACAGTTTCCG CTCCACAGG-3' | 8 |
| NTRK3 | Forward | 5'-CATAAGATTCTAG AATGATGTCTCTCTTT GCCAG-3' | 9 |
| | Reverse | 5'-CAGATCCTGCGGC GCTTAAAAGCCATGAC GTCCTTTGCTGA-3' | 10 |
| ERC1 | Forward | 5'-CATAGAAGATTCT AGAATGTATGGAAGTG CCCGCTC-3' | 11 |
| | Reverse | 5'-CAGATCCTTGCGG CCGCTCAAGAGGACTC TTCCAGGGCG-3' | 12 |

3-3: Analysis of LCN2 Expression by Sorafenib Treatment

Vector, SULF2-WT and SULF2-N491K cells were treated with sorafenib to identify LCN2 mRNA expression.

As a result, sorafenib treatment significantly induced LCN2 mRNA expression in SULF2-WT cells, but induced only a small amount of LCN2 expression in vector and SULF2-N491K cells (FIG. 4C). This means different regulation of sorafenib between cells expressing wild-type SULF2 and cells expressing mutant SULF2.

In order to further identify this, SULF2-WT cells were transfected with two different shRNAs further targeting LCN2, SULF2-WT-LCN2sh-252 and SULF2-WT-LCN2sh-459.

As a result, the knockdown of LCN2 by shRNA significantly reduced susceptibility to sorafenib in SULF2-WT cells at $IC_{50}$ from 7.51 μM to 3.95 μM (FIG. 4D), reducing the cell growth rate by about 30%. In conclusion, these results suggest that LCN2 mediates sorafenib sensitization associated with SULF2 expression.

Example 4: EGFR/STAT1 and NF-kB Signaling Associated with SULF2-Mediated LCN2 Expression 4-1: Signal Pathway Induced by SULF2

LCN2 expression is induced by STAT1 and NF-κB signals through activation of EGFR (Viau A et al., J. Clin. Invest. 120:4065-76, 2010; Zhao P et al., Mol. Metab. 2:161-70, 2013). Thus, whether or not the EGFR/STAT1 and NF-κB signaling pathways were induced by SULF2 in liver cancer cells was identified.

In order to prepare total cell lysate, cells were lysed in a high-salt-content lysis buffer (20 mM Tris-HCl [pH 8.0], 1% Triton X-100, 2 mM EDTA and 1 mM phenylmethylsulfonyl fluoride), incubated on ice for 20 minutes, and centrifuged for 20 minutes to remove cell debris. A total of 20 μg of total cell lysate was used for SDS-polyacrylamide gel electrophoresis, and proteins were transferred to a nitrocellulose membrane and incubated overnight with each antibody at 4° C. The membrane was then incubated at room temperature for 1 hour with a peroxidase-conjugated secondary antibody (PIERCE, Rockford, Ill., USA), and signals were detected using a chemiluminescence detection kit (PIERCE).

Figure 5:
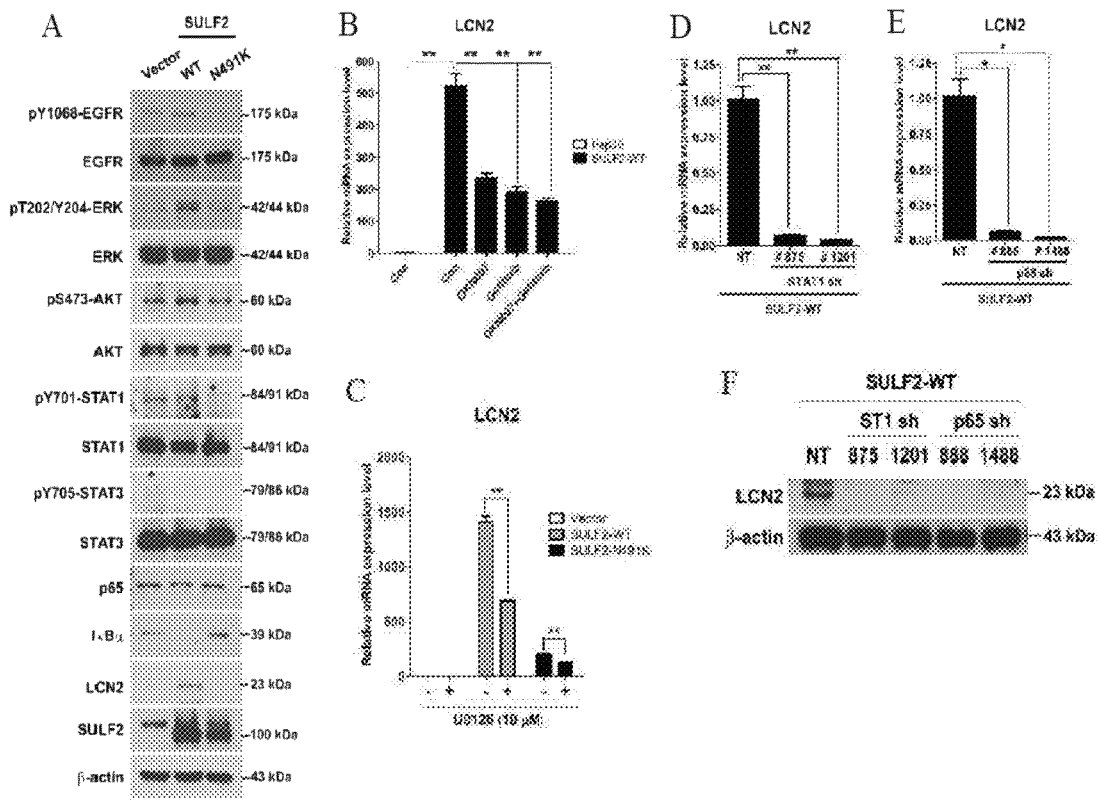
FIG. 5A shows the protein expression found in vector, SULF2-WT and SULF2-N491K cells.
FIG. 5B shows LCN2 mRNA expression levels measured by qRT-PCR after exposure of SULF2-WT cells to OKN-007 (200 μM) and/or gefitinib (5 μM) for 48 hours.
FIG. 5C shows LCN2 mRNA expression levels measured by qRT-PCR after exposure of vector, SULF2-WT and SULF2-N491K cells to U0126 (10 μM) for 48 hours.
FIGS. 5D and 5E show expression levels of LCN2 mRNA measured by qRT-PCR in SULF2-WT cells expressing NT shRNA, STAT1 shRNA (#875 or #1201) or p65 shRNA (#888 or #1488)
FIG. 5F shows the identification result using Western blotting.

As a result, expression of the active forms of EGFR, AKT, ERK and STAT1 was increased in SULF2-WT cells, but was not increased in the vector and SULF2-N491K cells. In addition, since the expression of IκBα protein was reduced in SULF2-WT cells compared to other cell types, the NF-κB signal was activated in SULF2-WT cells, but not activated in SULF2-N491K cells. NF-κB p65 subunit levels did not change in the tested cells. The STAT3 pathway (Xu M J et al., Hepatology 61: 692-702, 2015), which induced LCN2 production after bacterial infection or partial hepatectomy, was also found, but significant activation of STAT3 was detected in none of the tested cells (FIG. 5A).

In conclusion, it can be seen that SULF2 regulates the EGFR/STAT1 and NF-κB signaling pathways, but STAT3 does not regulate the same.

4-2: Signaling Pathway Involved in SULF-Mediated LCN2 Expression

Next, whether or not the STAT1 and NF-κB signals were involved in SULF-mediated LCN2 expression was identified.

When SULF2-WT cells were treated with a SULF2 inhibitor (OKN-007, 200 μM) or an EGFR inhibitor (gefitinib, 5 μM), both inhibitors significantly inhibited LCN2 mRNA expression. In addition, treatment with a combination of OKN-007 and gefitinib resulted in an increase in the inhibition of LCN2 (FIG. 5B). In addition, since EGFR/MAP (ERKs 1 and 2) pathway induces LCN2 expression (Zhao P et al., Mol Metab 2:161-70, 2013; Ding G et al., Prostate 75:957-68, 2015), treatment with a MEK inhibitor significantly inhibited LCN2 expression in SULF2-WT cells, but did not inhibit the same in vector or SULF2-N491K cells (FIG. 5C). Then, STAT1 shRNA or p65 shRNA was transfected into SULF2-WT cells, and STAT1 and NF-κB signals were investigated. As a result, LCN2 expression was significantly suppressed at the mRNA and protein levels (FIGS. 5D to 5F).

In conclusion, this suggests that SULF2-mediated LCN2 expression is possible through activation of EGFR/STAT1, MAPK and NF-κB.

Example 5: Mechanism of EGFR Signals in SULF2-WT and SULF2-N491K Cells

5-1: EGFR Differential Regulation in SULF2-WT and SULF2-N491K

EGFR signaling is a major signaling pathway associated with the effect of sorafenib on cancer cell growth. The expression of amphiregulin, the EGFR ligand, is also increased in HCC patients undergoing treatment with sorafenib and HCC cell lines (Blivet-Van Eggelpoel M J et al. J. Hepatol. 57: 108-15, 2012). This amphiregulin expression is significantly increased in the vector, SULF2-WT and SULF2-N491K cells after treatment with sorafenib, indicating that EGFR is activated by sorafenib (FIG. 6A).

Thus, in order to elucidate the mechanism by which sorafenib-mediated EGFR activation is differentially regulated between SULF2-WT and SULF2-N491K, the effect of exogenous stimulation of EGFR by treatment with recombinant human amphiregulin (rhAR) on three types of cells was compared.

As a result, elevated activation of the downstream signaling pathways of EGFR and EGFR including STAT1 and ERK was found in SULF2-WT through treatment with amphiregulin, but was not found in the vector or SULF2-N491K cells. It was found that the AKT/NF-κB signal was activated in SULF2-WT, but was not activated in SULF2-N491K cells. IκBα protein levels were much higher in SULF2-WT cells than in vector and SULF2-N491K cells. Treatment with amphiregulin significantly increased p65 and LCN2 protein levels in SULF2-WT cells (FIG. 6B). That is, these results suggest that SUFL2-induced LCN2 expression is mediated by the activation of the EGFR signal through the downstream pathway including MAPK, STAT1 and AKT/NF-κB signals.

The phosphorylation and downstream signaling activity of EGFR were reduced in SULF2-N491K cells (FIG. 6B), but the expression of amphiregulin induced by sorafenib was not significantly different between the three types of cells (FIG. 6A). Therefore, the enzymatic activities of SULF2-WT and SULF2-N491K were compared (Biovision, Milpitas, Calif., USA).

Hep3B cells ($2\times10^6$ cells/ml) expressing vector, SULF2-WT or SULF2-N491K cells were homogenized in PBS containing a protease inhibitor and centrifuged at 10,000 g at 4° C. for 10 minutes to collect the supernatant. 10 µl of the supernatant was transferred to a 96-well plate containing 90 µl of a reaction mixture (50 µl of sulfatase assay buffer and 40 µl of sulfatase substrate), incubated at 37° C. for 30 minutes and then detected with a microplate reader (OD 515 nm). All experiments were repeated at least 3 times for each sample.

As a result, there was no significant difference in the enzymatic activity of sulfatase (FIG. 7D).

5-2: Interaction Between Amphiregulin and EGFR

The direct interaction between amphiregulin and EGFR was assessed through confocal microscopy analysis.

In order to detect the coexistence of proteins, cells were grown on a Lab-Tek four-well glass chamber slide (NUNC, Rockford, Ill., USA). After culture for 24 hours, the cells were fixed, permeabilized for 5 minutes using cold methanol, washed with phosphate-buffered saline (PBS) and then incubated with primary antibody and secondary antibody conjugates. In order to detect cell surface optimization of SULF2, the cells were cultured with SULF2 antibody in serum-free DMEM for 1 hour at 4° C., washed with PBS and fixed with 4% paraformaldehyde. After blocking with 2% fetal bovine serum, the cells were labeled with a donkey anti-mouse IgG second antibody and conjugated with Alexa-594. Images were collected using a 40× water-immersion objective lens in a laser scanning confocal microscope LSM710 (Carl Zeiss, Oberkochen, Germany) equipped with argon (488 nm) and krypton (568 nm) lasers. The images were processed using a ZEN 2009 light edition (Carl Zeiss).

As a result, in the vector cells, EGFR and amphiregulin were diffused throughout the cytoplasm, but coexisted around the nucleus when treated with sorafenib (FIG. 7A). In SUFL2-WT cells, EGFR and amphiregulin already coexisted, which was increased by treatment with sorafenib. In contrast, SULF2-N491K cells did not show increased coexistence upon treatment with sorafenib. In conclusion, this suggests that EGFR activation induced by SULF2 is mediated by promoting the interaction between amphiregulin and EGFR. In other words, functional changes in SULF2-N491K cells impair this interaction to inhibit EGFR signaling.

Next, since the N491K mutation of SULF2 protein is positioned in the hydrophilic domain (HD), which is essential for cell surface localization of SULF2 (Frese M A et al., J Biol Chem 284:28033-44, 2009; Tang R et al., J Biol Chem 284:21505-14, 2009), whether or not the SULF2 mutation can affect the position of protein on the cell surface was investigated through confocal microscopy.

As a result, SULF2-WT was widely distributed on the cell surface, while SULF2-N491K was not well maintained in the membrane (FIG. 7B). Immunofluorescence analysis of permeabilized cells showed strong cell staining in SULF2-WT and SULF2-N491K (FIG. 7C). That is, even when the mutated SULF2 is enzymatically active, the SULF2 protein is not localized on the cell surface, thus resulting in impaired interactions between amphiregulin and EGFR in SULF2-N491K cells.

Example 6: Effect of SULF2 Expression and Mutation on Growth and Migration of Cancer Cells

6-1: Cell Proliferation and Migration of SULF2-WT or SULF2-N491K

The effect of SULF2-WT or SULF2-N491K on cell proliferation and migration was investigated.

For cell proliferation analysis, $5\times10^3$ cells were divided into 96-well plates and cultured in DMEM containing various concentrations of anti-cancer drugs and 5% FBS for 48 hours. Cell viability was measured through WST-1 assay (Roche, Gangnam-gu, Seoul, Korea) and four repetitions of each experiment were performed at least 3 times. Cell migration analysis was performed in a 24-well Boyden chamber (8 µm pore size; Coastal; Corning Life Sciences, Lowell, Mass.), $1\times10^5$ cells were suspended in serum-free 0.2 ml DMEM and added to the upper chamber inlet, and the lower chamber was filled with 0.6 ml DMEM/10% fetal bovine serum. After 6 hours, the cells on the bottom of the membrane were fixed, stained and counted at ×200 magnification with four microscopes.

Figure 8A:
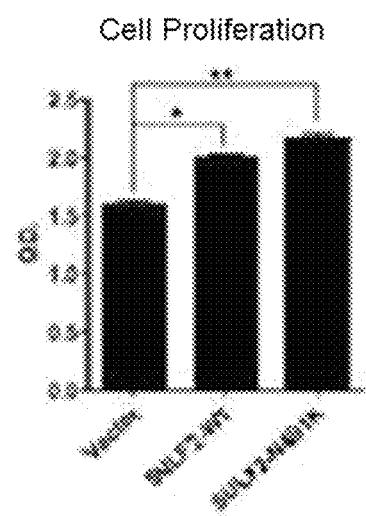
FIG. 8A shows the proliferation rate measured after culturing vector, SULF2-WT and SULF2-N491K cells for 48 hours.
Figure 8B:
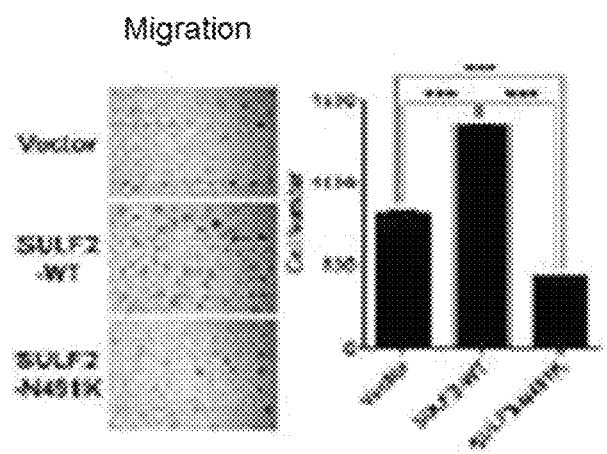
FIG. 8B shows the effects of SULF2-WT or SULF2-N491K on Hep3B cell migration measured using a Transwell migration assay system.

As a result, SULF2-WT and SULF2-N491K cells were found to grow faster than vector cells (FIG. 8A). In addition, the SULF2-WT cells showed significantly increased cell migration, whereas SULF2-N491K cells were less mobile than vector cells (FIG. 8B). This indicates that the regulation of cell growth and migration between SULF2-WT cells and SULF2-N491K cells may be different.

In this regard, FGF2 is known to stimulate the proliferation of HCC through self-secretion mechanisms (Wang L et al., Mol. Cancer. Ther. 11:864-72, 2012; Sandhu D S et al., Hepatology 59:1166-73, 2014). The FGF2 signal is activated by the formation of three complexes of functional FGF/FGFR/HS. SULF catalyzes the 6-O-desulphurisation of HS, which affects the binding of HS to FGF2, to prevent the production of FGF signaling complexes (Vines R R et al., Front. Oncol. 3: 331, 2014). Thus, the activity of phosphorylated FGFR and cell proliferation by FGF2 inhibition were identified.

Figure 8C:
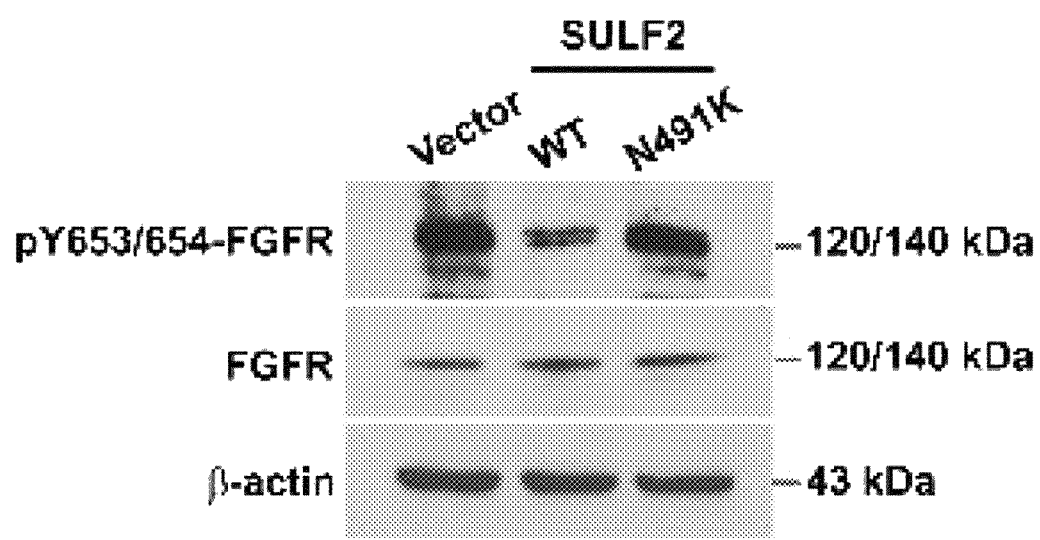
FIG. 8C shows Western blotting analysis of EFGR and phosphorylated EGFR in cultured cells.
Figure 8D:
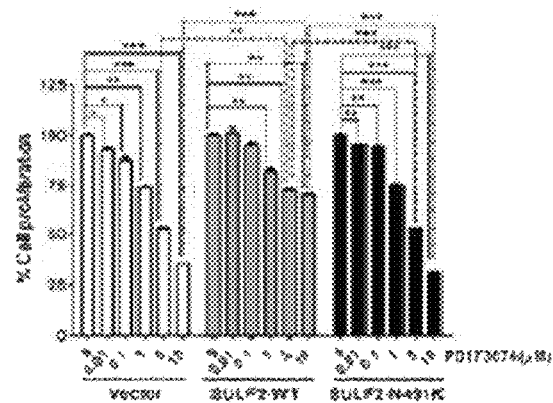
FIG. 8D shows cell viability measured after culturing vector, SULF2-WT or SULF2-N491K cells together with PD173074 (0.01, 0.1, 1, 5 or 10 μM) for 48 hours.
Figure 8E:
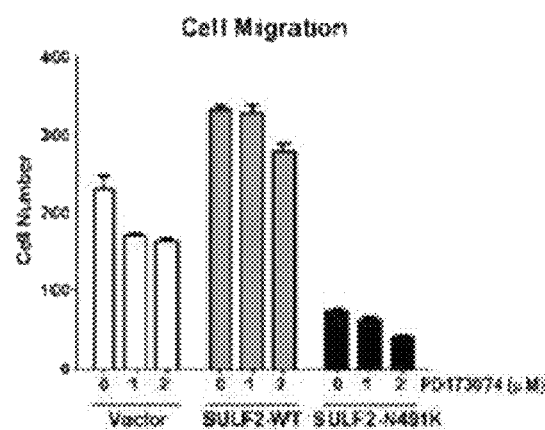
FIG. 8E shows the effect of PD173074 on cell migration analyzed using the Transwell migration assay system.

As a result, it was found that the activity of phosphorylated FGFR was higher in SULF2-N491K cells than in SULF2-WT cells (FIG. 8C). In addition, it was found that treatment with the FGF2 inhibitor, PD173074 inhibited cell proliferation in vector and SULF2-N491K cells in a concentration-dependent manner, but did not inhibit the same in SULF2-WT cells (FIG. 8D). However, the inhibition of great migration was not found in cells treated with PD173074 (FIG. 8E). Thus, this suggests that increased activity of FGF2 in SULF2-N491K can cause accelerated proliferation of these cells. However, FGF2 may not play an important role in mediation of migration.

6-2: Effect of EGFR Signaling on Proliferation and Migration

The effect of EGFR signaling on the proliferation and migration of SULF2-WT and SULF2-N491K cells was investigated.

Figure 8F:
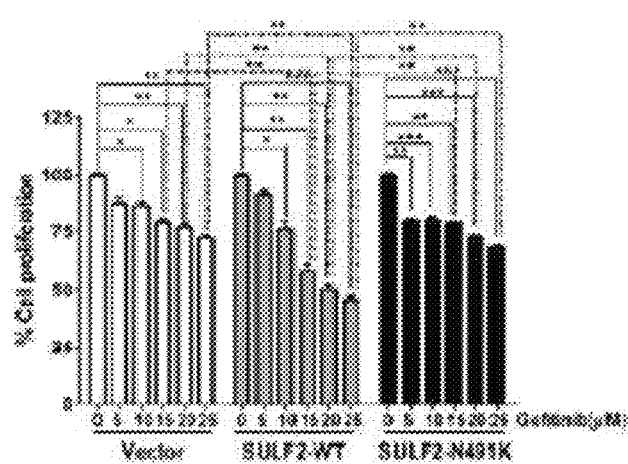
FIG. 8F shows cell viability measured after culturing vector, SULF2-WT or SULF2-N491K cells together with gefitinib (0.5, 10, 15, 20 or 25 μM) for 48 hours.
Figure 8G:
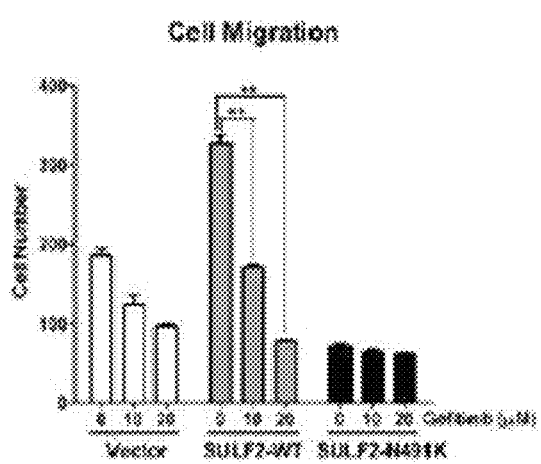
FIG. 8G shows the effect of gefitinib on cell migration analyzed using the Transwell migration assay system.

The result revealed that cell growth and migration were significantly inhibited in SULF2-WT cells treated with gefitinib as compared with the vector and SULF2-N491K cells (FIGS. 8F and 8G). That is, EGFR activation by SULF2 promoted cell growth and migration in SULF2-WT, but did not promote the same in SULF2-N491K cells. These results suggest that SULF2-N491K cells have high FGF2 activity, while SULF2-WT cells have high EGFR activity. The results showed that SULF2-WT cells had higher growth rate and migration activity (mobility), whereas SULF2-N491K cells had a higher growth rate, but less migration activity than vector cells.

Example 7: Reduction of Sorafenib Resistance by LCN2 or SULF2 Inhibition 7-1: SULF2 Inhibition Acquisition of resistance to sorafenib treatment is one of the major obstacles to the management of patients with liver cancer (Berasain et al., Gut 62: 1674-5, 2013; Chow A K et al., PLoS One 8: e78675, 2013). Thus, whether or not changes in SULF2 and LCN2 expression were capable of relieving sorafenib resistance was investigated. First, sorafenib-resistant cells were established by continuously exposing Hep3B cells to a gradually increasing concentration of sorafenib (up to 5 µM). After culture for several months, the sorafenib-resistant (SR) cell lines, Vector-SR, SULF2-WT-SR and SULF2-N491K-SR were obtained.

Figure 9A:
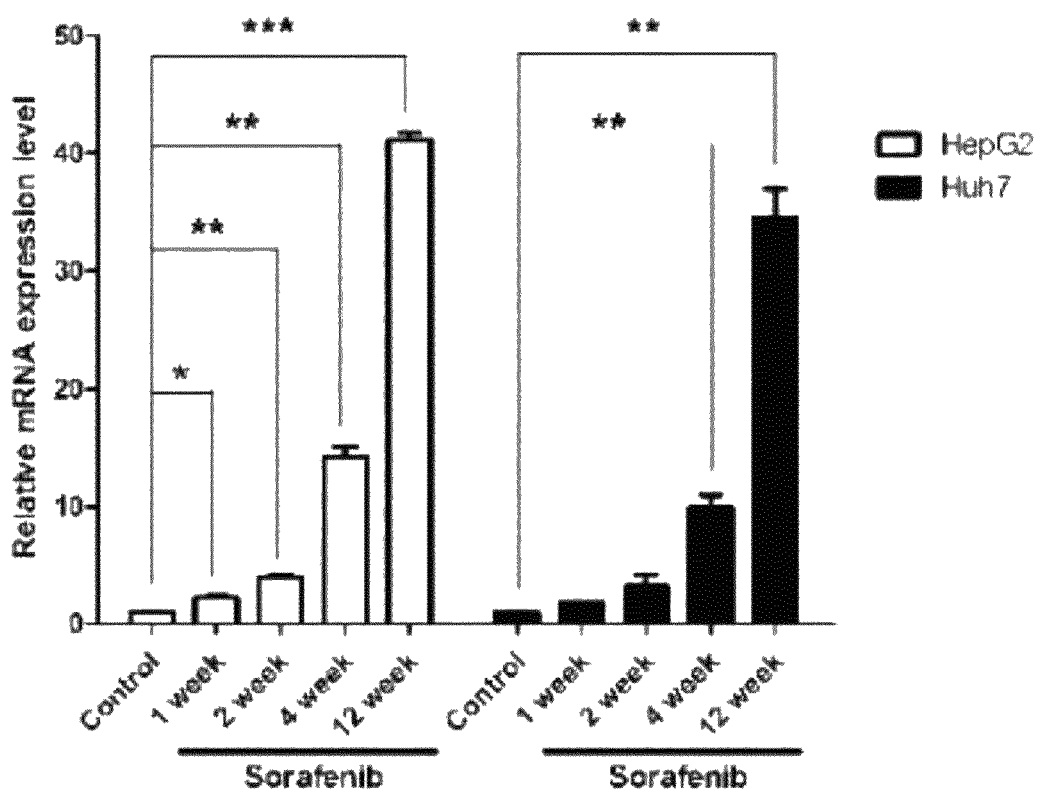
FIG. 9A shows SULF2 mRNA expression levels measured by qRT-PCR after treating HepG2 and Huh7 cells with sorafenib (up to 10 μM)

In order to investigate the effect of sorafenib on SULF2 expression, SULF2 mRNA expression levels were measured while treating HepG2 and Huh7 cells with sorafenib (up to 10 µM) for 1, 2, 4 and 12 weeks. As a result, SULF2 mRNA expression was found to be significantly increased in a time-dependent manner by sorafenib treatment (FIG. 9A).

Figure 9B:
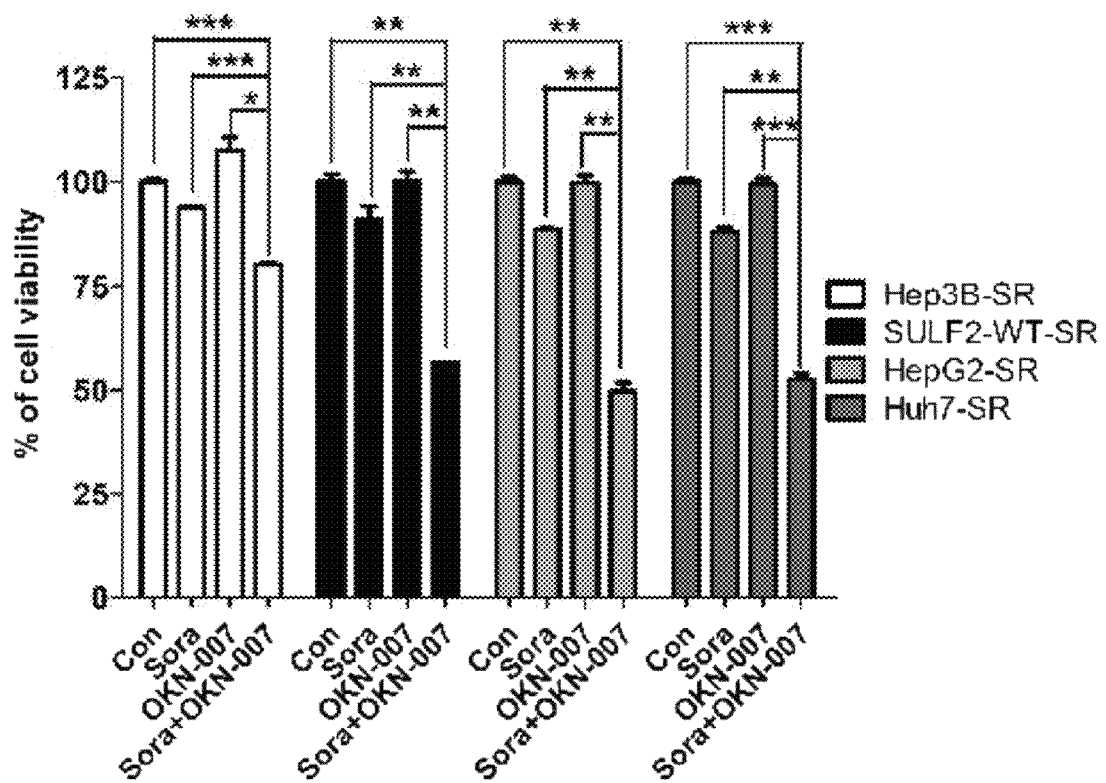
FIG. 9B shows the cell viability of Hep3B-SR, SULF2-WT-SR, HepG2-SR and Huh7-SR cells measured after treating with sorafenib (5 μM) and/or OKN-007 (200 μM) for 72 hours.

Thus, the treatment with a combination of sorafenib and OKN-007, the SULF2 inhibitor, to relieve sorafenib resistance resulted in increased susceptibility of sorafenib-resistant cells (FIG. 9B).

7-2: LCN2 Inhibition

Figure 9C:
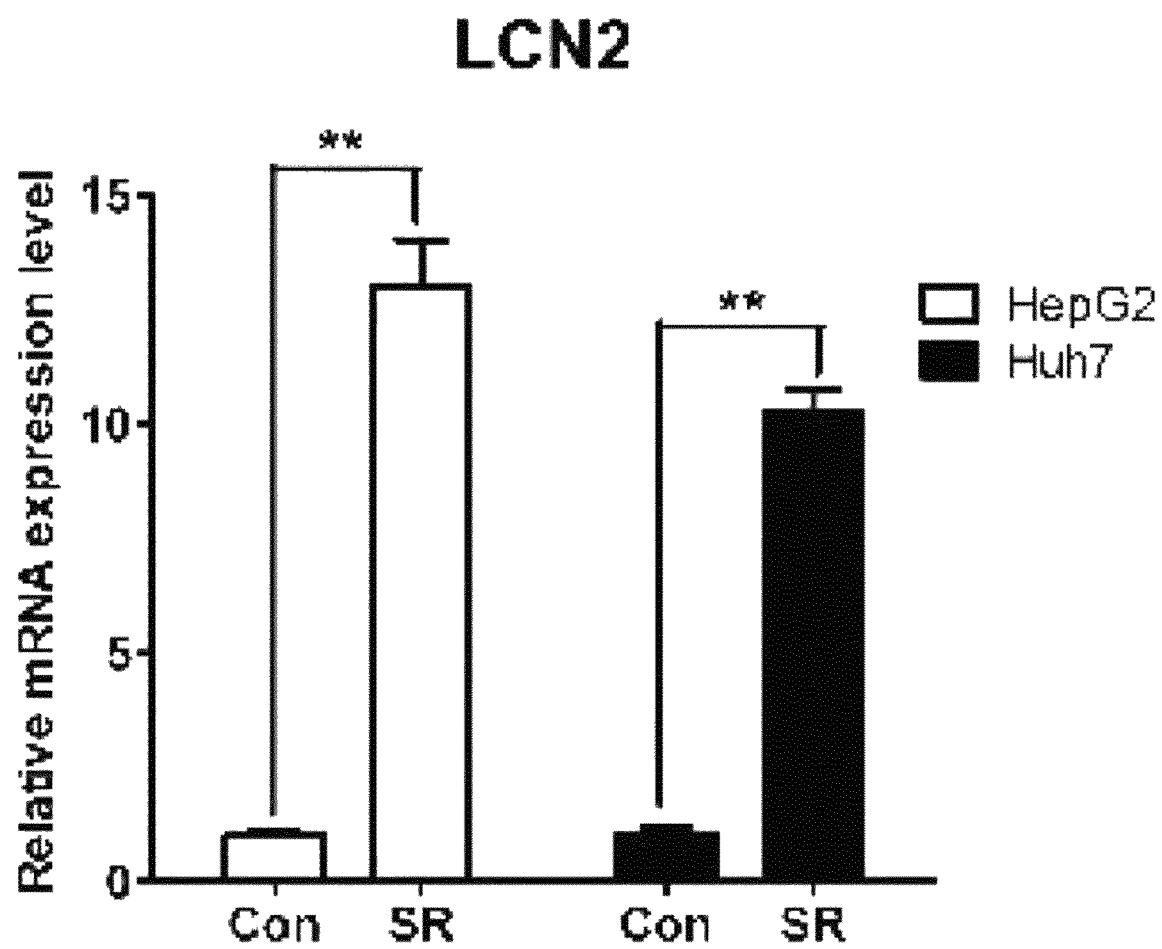
FIG. 9C shows SULF2 mRNA expression levels measured by qRT-PCR after culturing HepG2, Huh7, sorafenib-resistant HepG2 (HepG2-SR) and sorafenib-resistant Huh7 (Huh7-SR) cells.
Figure 9D:
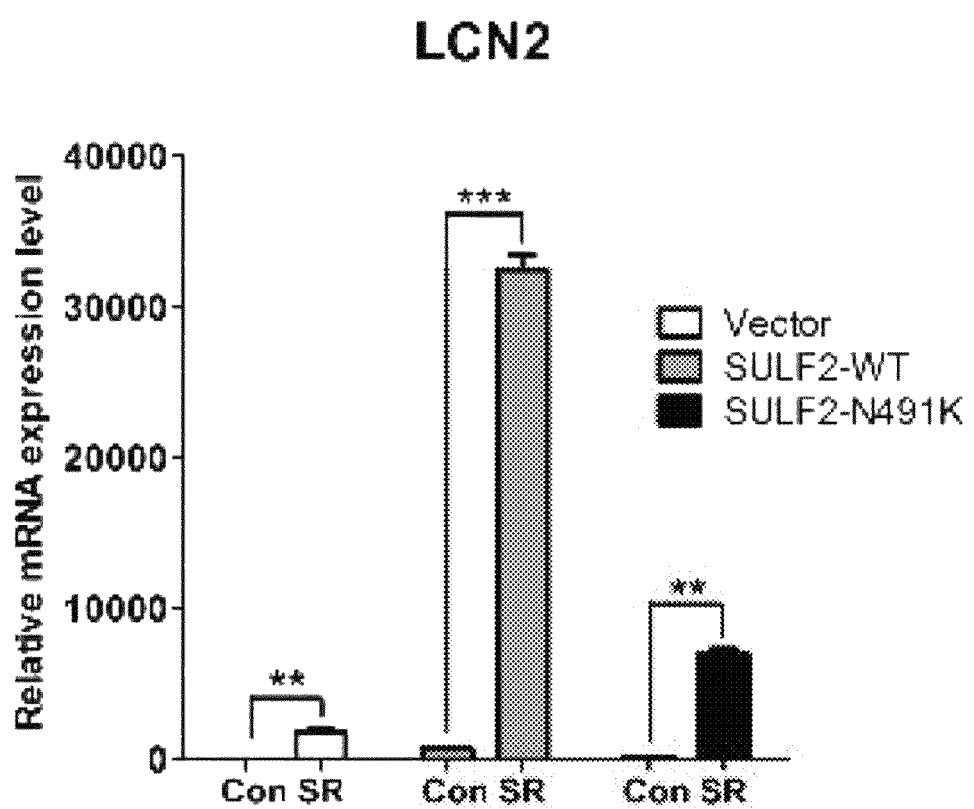
FIG. 9D shows SULF2 mRNA expression levels measured by qRT-PCR after culturing vector, SULF2-WT, SULF2-WT, SULF2-N491K, sorafenib-resistant vector (vector-SR), sorafenib-resistant SULF2-WT (SULF2-WT-SR) and sorafenib-resistant SULF2-N491K (SULF2-N491K-SR) cells.

In addition, it was found that sorafenib-resistant HepG2 (HepG2-SR) and sorafenib-resistant Huh7 cells (Huh7-SR) significantly overexpressed LCN2 compared to parent cells (FIG. 9C). Surprisingly, it was found that the sorafenib-resistant clone of SULF2-expressing Hep3B cells strongly expressed LCN2 up to 60 times the level of expression in the parental cells (FIG. 9D). Thus, it can be seen that sorafenib resistance induces LCN2 expression in liver cancer cells.

Figure 9E:
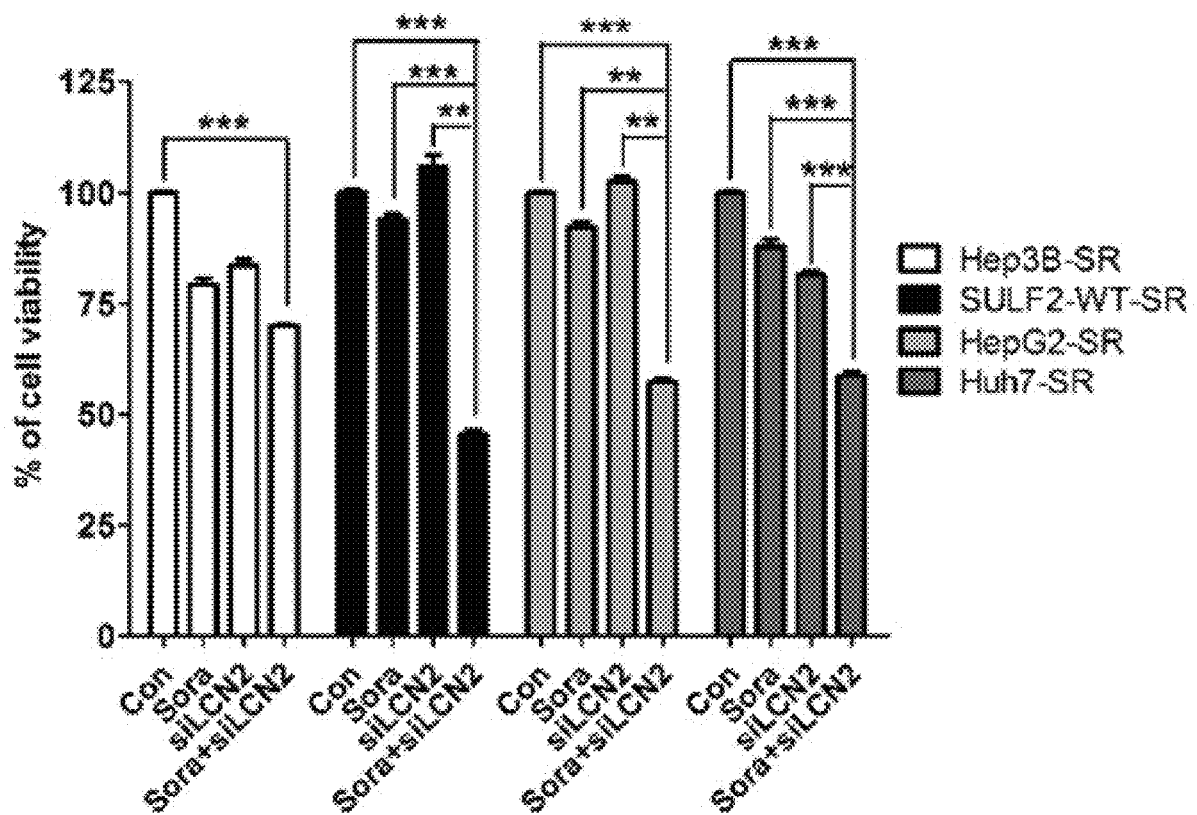
FIG. 9E shows the cell viability of Hep3B-SR, SULF2-WT-SR, HepG2-SR and Huh7-SR cells after transient transfection with LCN2 siRNA for 24 hours and then exposure to 5 μM sorafenib for 48 hours.

Thus, control siRNA and siRNA for human LCN2 were purchased from Santa Cruz Biotechnology, and each cell was transfected with siRNA using a transfection reagent (Santa Cruz) according to the manufacturer's instructions. LCN2 expression was knocked down through mediation of siRNA, thus resulting in restoration of sorafenib susceptibility and inhibition of growth when treated with sorafenib (FIG. 9E).

In conclusion, these results suggest that SULF2 and LCN2 expression play an important role in acquiring susceptibility to sorafenib. In particular, the combination of sorafenib and a SULF2 inhibitor may offer a new therapeutic strategy to patients resistant to sorafenib.

INDUSTRIAL APPLICABILITY

The method of predicting susceptibility to treatment with sorafenib using SULF2 genes according to the present invention can achieve an optimal therapeutic effect by administering an appropriate drug to cancer patients, and a composition for the treatment of sorafenib-resistant cancer through inhibition of SULF2 has a potent anticancer treatment effect.

Although specific configurations of the present invention have been described in detail, those skilled in the art will appreciate that this description is provided as preferred embodiments for illustrative purposes and should not be construed as limiting the scope of the present invention. Therefore, the substantial scope of the present invention is defined by the accompanying claims and equivalents thereto.

SEQUENCE LIST FREE TEXT

An electronic file is attached.

The invention claimed is:

1. A method for treating cancer in a subject in need thereof, comprising administering siRNAs or shRNAs that hybridize to a SULF (sulfatase 2) transcript and degrade the transcript to the subject, wherein the cancer is liver cancer resistant to sorafenib.

2. The method according to claim 1, which further comprises a radiation therapy or an anticancer agent treatment.

3. The method according to claim 2, wherein the anticancer agent is selected from the group consisting of OKN-007, gefitinib, doxorubicin, vinblastine, taxol, etoposide, cisplatin, 5-FU, ifosfamide, and combinations thereof.

4. The method according to claim 1, further comprises a step of measuring an expression level of mRNA of a SULF2 (sulfatase 2) gene or a level of protein encoded by the SULF2 gene, in a biological sample of the subject.

* * * * *

SEQUENCE LISTING

```
<160> NUMBER OF SEQ ID NOS: 12

<210> SEQ ID NO 1
<211> LENGTH: 30
<212> TYPE: DNA
<213> ORGANISM: Artificial Sequence
<220> FEATURE:
<223> OTHER INFORMATION: SULF2-F

<400> SEQUENCE: 1
```
catagaagat tctagaatgg gccccccgag                                                    30

<210> SEQ ID NO 2
<211> LENGTH: 37
<212> TYPE: DNA
<213> ORGANISM: Artificial Sequence
<220> FEATURE:
<223> OTHER INFORMATION: SULF2-R

<400> SEQUENCE: 2
cagatccttg cggccgctca accttcccag ccttccc                                            37

<210> SEQ ID NO 3
<211> LENGTH: 20
<212> TYPE: DNA
<213> ORGANISM: Artificial Sequence
<220> FEATURE:
<223> OTHER INFORMATION: LCN2-F

<400> SEQUENCE: 3
cagcagaact tccaggacaa                                                               20

<210> SEQ ID NO 4
<211> LENGTH: 20
<212> TYPE: DNA
<213> ORGANISM: Artificial Sequence
<220> FEATURE:
<223> OTHER INFORMATION: LCN2-R

<400> SEQUENCE: 4
taaacaggac ggaggtgaca                                                               20

<210> SEQ ID NO 5
<211> LENGTH: 20
<212> TYPE: DNA
<213> ORGANISM: Artificial Sequence
<220> FEATURE:
<223> OTHER INFORMATION: Amphiregulin-F

<400> SEQUENCE: 5
gctgtcgctc ttgatactcg                                                               20

<210> SEQ ID NO 6
<211> LENGTH: 20
<212> TYPE: DNA
<213> ORGANISM: Artificial Sequence
<220> FEATURE:
<223> OTHER INFORMATION: Amphiregulin-R

<400> SEQUENCE: 6
aatccatcag cactgtggtc                                                               20

<210> SEQ ID NO 7
<211> LENGTH: 33
<212> TYPE: DNA
<213> ORGANISM: Artificial Sequence
<220> FEATURE:
<223> OTHER INFORMATION: SHC1-F

<400> SEQUENCE: 7
catagaagat tctagaatgg atctcctgcc ccc                                                33

<210> SEQ ID NO 8
<211> LENGTH: 38
<212> TYPE: DNA
<213> ORGANISM: Artificial Sequence

```
<220> FEATURE:
<223> OTHER INFORMATION: SHC1-R

<400> SEQUENCE: 8
cagatccttg cggccgctca cagtttccgc tccacagg                              38

<210> SEQ ID NO 9
<211> LENGTH: 34
<212> TYPE: DNA
<213> ORGANISM: Artificial Sequence
<220> FEATURE:
<223> OTHER INFORMATION: NTRK3-F

<400> SEQUENCE: 9
cataagattc tagaatgatg tctctctttg ccag                                  34

<210> SEQ ID NO 10
<211> LENGTH: 41
<212> TYPE: DNA
<213> ORGANISM: Artificial Sequence
<220> FEATURE:
<223> OTHER INFORMATION: NTRK3-R

<400> SEQUENCE: 10
cagatcctgc ggcgcttaaa agccatgacg tcctttgctg a                          41

<210> SEQ ID NO 11
<211> LENGTH: 36
<212> TYPE: DNA
<213> ORGANISM: Artificial Sequence
<220> FEATURE:
<223> OTHER INFORMATION: ERC1-F

<400> SEQUENCE: 11
catagaagat tctagaatgt atggaagtgc ccgctc                                36

<210> SEQ ID NO 12
<211> LENGTH: 39
<212> TYPE: DNA
<213> ORGANISM: Artificial Sequence
<220> FEATURE:
<223> OTHER INFORMATION: ERC1-R

<400> SEQUENCE: 12
cagatccttg cggccgctca agaggactct tccagggcg                             39
```